(12) United States Patent
Kawaminami et al.

(10) Patent No.: US 8,247,189 B2
(45) Date of Patent: Aug. 21, 2012

(54) MODIFIED FLAVIN ADENINE DINUCLEOTIDE-DEPENDENT GLUCOSE DEHYDROGENASE

(75) Inventors: Hiroshi Kawaminami, Fukui (JP);
Masao Kitabayashi, Fukui (JP);
Yoshiaki Nishiya, Fukui (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 13/421,207

(22) Filed: Mar. 15, 2012

(65) Prior Publication Data

US 2012/0171708 A1 Jul. 5, 2012

Related U.S. Application Data

(63) Continuation-in-part of application No. PCT/JP2010/065984, filed on Sep. 15, 2010.

(30) Foreign Application Priority Data

| Sep. 16, 2009 | (JP) | 2009-214579 |
| Oct. 9, 2009 | (JP) | 2009-235311 |
| Nov. 6, 2009 | (JP) | 2009-255152 |
| Dec. 25, 2009 | (JP) | 2009-293853 |
| Dec. 28, 2009 | (JP) | 2009-297965 |
| Mar. 26, 2010 | (JP) | 2010-071348 |

(51) Int. Cl.
*C12N 15/00* (2006.01)
*C12N 1/20* (2006.01)
*C12Q 1/00* (2006.01)
*C12Q 1/54* (2006.01)

(52) U.S. Cl. ............ 435/14; 204/403.14; 536/23.1; 435/320.1; 435/252.3; 435/190

(58) Field of Classification Search ............ 435/14, 435/190, 320.1, 252.3; 204/403.14
See application file for complete search history.

(56) References Cited

U.S. PATENT DOCUMENTS

| 2006/0063217 A1 | 3/2006 | Omura et al. |
| 2008/0220460 A1 | 9/2008 | Kawaminami et al. |
| 2008/0248514 A1 | 10/2008 | Inamori et al. |
| 2011/0033880 A1 | 2/2011 | Yada et al. |

FOREIGN PATENT DOCUMENTS

| EP | 1862543 | 12/2007 |
| JP | 2000-262297 | 9/2000 |
| JP | 2007-289148 | 11/2007 |
| JP | 2008-237210 | 10/2008 |
| JP | 2009-159964 | 7/2009 |
| WO | 2004/058958 | 7/2004 |
| WO | 2006/101239 | 9/2006 |
| WO | 2008/001903 | 1/2008 |
| WO | 2008/059777 | 5/2008 |
| WO | 2008/102639 | 8/2008 |

OTHER PUBLICATIONS

Bak, T.G. et al., Studies on the glucose dehydrogenase of *Aspergillus oryzae*, Biochim. Biophys. Acta, 1967, vol. 139, No. 2, pp. 265-276.
Bak, T.G., Studies on glucose dehydrogenase of *Aspergillus oryzae*, Biochim. Biophys. Acta., 1967, vol. 139, No. 2, pp. 277-293.
Bak, T.G., Studies on glucose dehydrogenase of *Aspergillus oryzae*, Biochim. Biophys. Acta., 1967, vol. 146, No. 2, pp. 317-327.
Bak, T.G. et al., Studies on glucose dehydrogenase of *Aspergillus oryzae*, Biochim. Biophys. Acta., 1967, vol. 146, No. 2, pp. 328-335.
Hayano, K. et al., Purification and properties of 3-ketosucrose-forming enzyme from the cells of *Agrobacterium tumefaciens*, The Journal of Biological Chemistry, 1967, vol. 242, No. 16, pp. 3665-3672.
Tsugawa, W. et al., Purification of a marine bacterial glucose dehydrogenase from *Cytophaga marinoflava* and its application for measurement of 1,5-anhydro-D-glucitol, Applied Biochemistry and Biotechnology, 1996, vol. 56, pp. 301-310.
Yamazaki, I., Differentiation between SMBG devices and POCT-compatible blood glucose measurement devices, Devices, Reagents, 2009, vol. 32, No. 6, pp. 707-713.
International Search Report for PCT/JP2010/065984, dated Nov. 16, 2010.

*Primary Examiner* — Maryam Monshipouri
(74) *Attorney, Agent, or Firm* — Roylance, Abrams, Berdo & Goodman, L.L.P.

(57) ABSTRACT

Provided is an enzyme that is further advantageous in terms of practical aspects when compared to publicly known enzymes for blood sugar sensors, and that can be used in a blood sugar level measuring reagent A flavin adenine dinucleotide-dependent glucose dehydrogenase that has amino acid sequence including a specific amino acid in an amino acid sequence shown in SEQ ID NO:2 or an amino acid sequence that has 60% homology therewith, and that has an improved temperature dependency.

10 Claims, 2 Drawing Sheets

FIG. 2

[63.540% / 565 aa]    INT/OPT.Score : <    1462/  1874 >

```
  1' MKNTTTYDYI VVGGGTSGLV VANRLSENPD VSVLLLEAGA SVFNNPDVTN ANGYGLAFGS
     ****  * ********  *******  *  *  ** ****   **  ***  *** .**********
  1" MKYDYI  VIGGGTSGLA VANRLSEDPS VNVLILEAGG SVWNNPNVTN VNGYGLAFGS

61' AIDWQYQSIN QSYAGGKQQV LRAGKALGGT STINGMAYTR AEDVQIDVWQ KLGNEGWTWK
     ********* * * * *   ** **********  **********  *******  *   ** *****
 57" DIDWQYQSVN QPYGGNVSQV LRAGKALGGT STINGMAYTR AEDVQIDAWE TIGNTGWTWK

121' DLLPYYLKSE NLTAPTSSGV AAGAAYNPAV NGKEGPLKVG WSGSLASGNL SVALNRTFQA
     .* *** ***  *.* ** **.  . ** *.      .* **** *  .    .* **  . *******.
117" NLFPYYRKSE NFTVPTKSQT SLGASYEAGA HGHEGPLDVA FT-QIESNNL TTYLNRTFQG

181' AGVPWVEDVN GGKMRGFNIY PSTLDVDLNV REDAARAYYF PYDDRKNLHL LENTTANRLF
     *  ** **** *********  *  ***. ..   *  **********   ** . * ***   *  ** ***.
176" MGLPWTEDVN GGKMRGFNLY PSTVNLEEYV REDAARAYYW PYKSRPNLHV LLNTFANRIV

241' WKNGSAEEAI -ADGVEITSA DGKVTRVHAK KEVIISAGAL RSPLILELSG VGNPTILKKN
     *.....  ...* *,.******   .* . *  .. * ****.******  .**  ******  .*** .* .*
236" WDGEARDGDI TASGVEITSR NGTVRVINAE KEVIVSAGAL KSPAILELSG IGNPSVLDKY

300' NITPRVDLPT VGENLQDQFN NGMAGEGYGV LAGASTVTYP SISDVFGNET DSIVASLRSQ
     **  * *.***  *********  *  *   *    *     ..* *   * **   ..  ****  *   .*   .*.
296" NIPVKVNLPT VGENLQDQVN SHMDASGNTS ISGTKAVSYP DVYDVFGDEA ESVAKQIRAS

360' LSDYAAATVK VSNGHMKQED LERLYQLQFD LIVKDKVPIA EILFHPGGGN AVSSEFWGLL
     *  .. ****.*        . ...    **   .*  *****    .   * *  **   *  .  ****  * * . **. .   * * . **. **
356" LKQYAADTAQ ANGNIMKAAD LERLFEVQYD LIFKGRVPIA EVLNYPGSAT SVFAEFWALL

420' PFARGNIHIS SNDPTAPAAI NPNYFMFEWD GKSQAGIAKY IRKILRSAPL NKLIAKETKP
     *****   **   *  . *   . . *  ******* ,**  .**  ...  *** **.    *  **  ....  **. .*
416" PFARGSVHIG SSNPVEFPVI NPNYFMLDWD AKSYVAVAKY IRRSFESYPL SSIV-KESTP

480' GLSEIPATAA DEKWVEW-LK ANYRSNFHPV GTAAMMPRSI GGVVDNRLRV YGTSNVRVVD
     *  .  ** .*.  ... * **  ..  ********** ********. *  ******. **. *  ***. ******
475" GYDVIPRNAS EQSWKEWVFD KNYRSNFHPV GTAAMMPREI GGVVDERLNV YGTTNVRVVD

539' ASVLPFQVCG HLVSTLYAVA ERASDLIKED AKSA        (SEQ ID NO: 1)
     **********  **********  ***. ****. *  *
535" ASVLPFQVCG HLVSTLYAVA ERAADLIKAD AGRR        (SEQ ID NO: 3)
```

MODIFIED FLAVIN ADENINE DINUCLEOTIDE-DEPENDENT GLUCOSE DEHYDROGENASE

This application is a CIP of PCT/JP2010/065984, filed Sep. 15, 2010, which claims priority to the following Japanese applications: 2009-214579, 2009-235311, 2009-255152, 2009-293853, 2009-297965 and 2010-071348, filed Sep. 16, 2009, Oct. 9, 2009, Nov. 6, 2009, Dec. 25, 2009, Dec. 28, 2009 and Mar. 26, 2010 respectively.

TECHNICAL FIELD

The present invention relates to a modified flavin adenine dinucleotide-dependent glucose dehydrogenase, DNA encoding an amino acid sequence thereof, a vector containing the DNA, a transformant transformed with the vector, and a method for producing the modified FADGDH by culturing the transformant. Furthermore, the present invention relates to various technologies using a modified flavin adenine dinucleotide.

BACKGROUND ART

In recent years, incidence of diabetes has been displaying an upward trend every year. In Japan alone, a combined number of diabetics and potential diabetics is estimated to be ten million or more. Also due to a very high interest in lifestyle-related diseases, opportunities to self-manage blood sugar levels have been increasing. In response to such recent trend, it is important to develop technologies for self-measuring and managing blood sugar levels. Although many blood sugar measuring technologies have been put to practical use, electrochemical sensing is useful from the standpoints such as scaling down the amount of sample to a minute quantity, shortening a measuring time, and reducing the size of a device.

Enzymes whose substrate is glucose that exist in blood are utilized in a technique for sensing in blood sugar measuring technologies. Examples of such enzyme include glucose oxidase (EC 1.1.3.4). Glucose oxidase is advantageous in that it has a high specificity for glucose and is highly stable against heat. In a blood sugar sensor using glucose oxidase, measurement is performed by transferring, to an electrode via mediator, electrons generated in a process of oxidizing glucose so as to be converted into D-glucono-δ-lactone. However, glucose oxidase easily transfers protons generated in the reaction to blood-dissolved oxygen, which affects a measured value and thus has been problematic.

In order to avoid such a problem, pyrroloquinoline quinone-dependent glucose dehydrogenase (EC 1.1.5.2 (former EC 1.1.99.17)) has been used as an enzyme for blood sugar sensors. Hereinafter, pyrroloquinoline quinone-dependent glucose dehydrogenase is also represented as PQQGDH as appropriate. PQQGDH is advantageous in that it is not affected by the dissolved oxygen. However, PQQGDH has a low substrate specificity and has an activity also toward sugars other than glucose, such as maltose and lactose, and thereby, has been problematic since accurate measurement of glucose is difficult.

Therefore, flavin adenine dinucleotide is gathering attention as a glucose dehydrogenase that is not affected by dissolved oxygen and that has superior substrate specificity. Hereinafter, flavin adenine dinucleotide is represented as FAD as appropriate. Glucose dehydrogenase is represented as GDH as appropriate. Flavin adenine dinucleotide-dependent glucose dehydrogenase is represented as FADGDH. FADGDH is described in Non-patent Literature 1 to 6, and has been known for a long time.

Patent Literature 1 discloses a gene sequence and an amino acid sequence of an FADGDH derived from *Aspergillus terreus*. Patent Literature 2 discloses an FADGDH derived from *Aspergillus oryzae*. Patent Literature 3 discloses a modified FADGDH having an improved thermal stability, resulting from modifying an FADGDH derived from *Aspergillus oryzae*. Patent Literature 4 discloses a modified FADGDH having improved thermal stability and action to xylose, resulting from modifying an FADGDH derived from *Aspergillus oryzae* and an FADGDH derived from *Aspergillus terreus*. Patent Literature 5 discloses a glucose sensor using an FADGDH derived from *Aspergillus terreus*.

On the other hand, Non-patent Literature 7 indicates that, as a caution for SMBG (Self Monitoring Blood Glucose) devices, measured values obtained from many devices deviate from an acceptable range defined by ISO15197 in an environmental temperature condition such as in a low temperature range and a high temperature range, and may become a cause of medical accidents if the measured values show an extremely low value or a high value.

CITATION LIST

Patent Literature

PTL 1: WO 2004/058958
PTL 2: Japanese Patent Application No. 2007-289148
PTL 3: Japanese Patent Application No. 2008-237210
PTL 4: WO 2008/059777
PTL 5: WO 2006/101239

Non-Patent Literature

NPL 1: BIOCHIM BIOPHYS ACTA. 1967 Jul. 11; 139(2): 265-76
NPL 2: BIOCHIM BIOPHYS ACTA. 1967 Jul. 11; 139(2): 277-93
NPL 3: BIOCHIM BIOPHYS ACTA. 146(2): 317-27
NPL 4: BIOCHIM BIOPHYS ACTA. 146(2): 328-35
NPL 5: J BIOL CHEM (1967) 242: 3665-3672
NPL 6: APPL BIOCHEM BIOTECHNOL (1996) 56: 301-310
NPL 7: J CLIN LAB INST REAG 32(6), 2009: 707-713

SUMMARY OF INVENTION

Technical Problem

An objective of the present invention is to provide an enzyme that is further advantageous in terms of practical aspects when compared to publicly known enzymes for blood sugar sensors, and that can be used in a blood sugar level measuring reagent.

The present inventors have conducted examination focusing on abnormalities and variations of blood glucose levels caused by changes in the temperature of environments in which the levels are measured, and found that the following problems exist.

With regard to enzyme reaction conditions in a developmental stage, studies are performed centering on a specific temperature (for example, 37° C.). In contrast, room temperature is used by diabetics as the temperature for actually performing measurements of glucose using a glucose sensor. If fluctuation occurs in the reactivity of an enzyme due to temperature change, fluctuation occurs in measured values.

Correction functions that anticipate such reactivity fluctuation due to temperature are incorporated in some glucose sensors, however, such functions are not perfect.

Some publicly known FADGDHs have an action to xylose. Xylose is a monosaccharide that is used in digestion-and-absorption tests for carbohydrates. Therefore, when a patient undergoing a xylose absorption test uses a blood sugar sensor, the FADGDH react not only to blood glucose but also to xylose, and cause a problem where a measured value indicates a value higher than the right glucose level.

A publicly known FADGDH disclosed in Patent Literature 2 or Patent Literature 3 has a low specific activity for an enzyme to be used in a clinical test reagent, and has a disadvantage where a highly concentrated enzyme needs to be added for a clinical test.

Solution to Problem

Based on the above described examination, the present inventors have studied the temperature dependency of the publicly known FADGDH disclosed in Patent Literature 2 or Patent Literature 3. As a result, the present inventors have revealed that, with the FADGDH disclosed in Patent Literature 3, an activity value obtained at 25° C. is 63% and an activity value obtained at 5° C. is 40% when an activity value obtained at 37° C. is defined as 100%. In other words, it has been revealed that, depending on an environmental temperature used when measuring a glucose level, measurement precision of the FADGDH deteriorates. More specifically, there is a 37% reduction in activity from the activity value obtained at 37° C. to the activity value obtained at 25° C. Such activity fluctuation is a factor that prevents accurate measurement of glucose level using such an enzyme. This is because, for example, in some glucose sensors, glucose level is estimated based on an amount of a dehydrogenation product obtained from catalysis by GDH within a certain period of time.

In the present invention, an activity value at 25° C. of a pre-modified FADGDH is divided by an activity value thereof at 37° C. to obtain a value, and this value is converted so as to be 1; and a "temperature dependency value" for each modified object is obtained by dividing, by the value of the pre-modified FADGDH, a value that is obtained by similarly measuring activity values and performing a similar calculation.

If the temperature dependency value is 1.1, a calculated difference between those at 37° C. and 25° C. is about 30%, and a difference between those at 25° C. and 30° C. is estimated to be reduced to about 12-13%. When this is considered as a difference between a maximum value and a minimum value of data fluctuation, the temperature dependency value being 1.1 is preferable since this difference settles within about plus or minus 6-7%.

Further, if the temperature dependency is 1.2, a difference between those at 37° C. and 25° C. is about 24%, and a difference between those at 25° C. and 30° C. is estimated to be reduced to about 10%. When this is considered as a difference between a maximum value and a minimum value of data fluctuation, the temperature dependency being 1.2 is preferable since this difference settles within about plus or minus 5%.

Improvement in precision and accuracy of a measurement can be expected if the fluctuation of reactivity due to environmental temperature can be reduced. In the present application, smoothening of this optimum temperature peak is described as an improvement in temperature dependency.

The present inventors have conducted thorough research, and discovered, by substituting a specific amino acid in a publicly known FADGDH with another amino acid, a modified FADGDH whose temperature dependency has improved from that of a wild-type pre-modified FADGDH; and the present inventors have completed the present invention by setting up a glucose measurement system using the modified FADGDH.

In addition, the present inventors have examined the action to xylose of the FADGDH disclosed in Patent Literature 1 (cf. Patent Literature 4), and discovered that the FADGDH's action to xylose is about 10% when its reactivity toward glucose is defined as 100%. In other words, it was revealed that, measuring glucose level using this FADGDH has a disadvantage where accuracy of a measured value becomes impaired.

The present inventors have conducted thorough research, and discovered, by substituting a specific amino acid in a publicly known FADGDH with another amino acid, a modified FADGDH whose temperature dependency is improved from that of the pre-modified FADGDH and whose action to xylose is reduced; and completed the present invention.

In addition, the present inventors have found that the modified FADGDH, which is obtained by substituting an amino acid at a specific position of FADGDH with another amino acid, has an improved specific activity; and completed the present invention. The present inventors have made further improvements based on such findings, and completed the present invention.

In the following, representative modes of the present invention are shown.

Item A1. A protein of the following (A1) or (A2):

(A1) a protein having an amino acid sequence that contains, in an amino acid sequence shown in SEQ ID NO: 2, any of the amino acid substitutions set forth by the following (a):

(a) S60C, S60D, S60L, S60N, S60V, S60G, S60T, N504G, N504S, G59Y, G59F, G59M, G59T, G59C, G59L, G59H, G59K, G59Q, G59W, G59N, G59P, G59A, G59S, G59D, F58E, F58Q, F58S, F58T, F58A, F58I, F58M, F58Y, F58H, F58L, G53R, G53S, G53F, G53L, G53W, G53Y, and G53Q;

(A2) a protein that satisfies the following (i) to (iii);

(i) one having an amino acid sequence that contains, in an amino acid sequence having at least 60% homology with the amino acid sequence shown in SEQ ID NO: 2, an amino acid set forth by the following (b), (b) 60C, 60D, 60L, 60N, 60V, 60G, 60T, 504G, 504S, 59Y, 59F, 59M, 59T, 59C, 59L, 59H, 59K, 59Q, 59W, 59N, 59P, 59A, 59S, 59D, 58E, 58Q, 58S, 58T, 58A, 58I, 58M, 58Y, 58H, 58L, 53R, 53S, 53F, 53L, 53W, 53Y, and 53Q, (ii) one having a glucose dehydrogenase activity, and (iii) one having a temperature dependency that is superior to that of a protein having the amino acid sequence shown in SEQ ID NO: 2.

Item A2. The protein of (A1) according to item A1, wherein the amino acid substitution is any of the substitutions selected from the group consisting of S60C, S60D, S60L, N504G, N504S, G59Y, G59F, G59M, G59T, G59C, G59L, G59H, G59K, G59Q, G59W, G59N, F58E, F58Q, F58S, and F58T.

Item A3. The protein of (A2) according to item A1, wherein the protein includes any of the amino acids selected from the group consisting of 60C, 60D, 60L, 504G, 504S, 59Y, 59F, 59M, 59T, 59C, 59L, 59H, 59K, 59Q, 59W, 59N, 58E, 58Q, 58S, and 58T.

Item B1. A modified FADGDH that contains, in an amino acid sequence of an FADGDH shown in SEQ ID NO: 1 or SEQ ID NO: 2, an amino acid substitution at position 58 or at a position equivalent thereto, and that has an improved temperature dependency when compared to pre-modification.

Item B2. The modified FADGDH according to item B1, wherein the amino acid substitution is any of the substitutions selected from the group consisting of F58A, F58E, F58H, F58I, F58L, F58M, F58Q, F58S, F58T, and F58Y, or the modified FADGDH contains an equivalent amino acid substitution at a position equivalent thereto.

Item B3. A modified FADGDH that contains, in an amino acid sequence of an FADGDH shown in SEQ ID NO: 1 or SEQ ID NO: 2, an amino acid substitution at position 58 or at a position equivalent thereto, and that has a reduced action to xylose when compared to pre-modification.

Item B4. The modified FADGDH according to item B3, wherein the amino acid substitution is any of the substitutions selected from the group consisting of F58A, F58E, F58H, F58I, F58L, F58M, F58Q, F58S, F58T, and F58Y, or the modified FADGDH contains an equivalent amino acid substitution at a position equivalent thereto.

Item B5. A modified FADGDH that contains, in an amino acid sequence of an FADGDH shown in SEQ ID NO: 1 or SEQ ID NO: 2, an amino acid substitution at position 58 or at a position equivalent thereto, and that has an improved temperature dependency and a reduced action to xylose when compared to pre-modification.

Item B6. The modified FADGDH according to item B5, wherein the amino acid substitution is any of the substitutions selected from the group consisting of F58A, F58E, F58H, F58I, F58L, F58M, F58Q, F58S, F58T, and F58Y, or the modified FADGDH contains an equivalent amino acid substitution at a position equivalent thereto.

Item C1. A modified FADGDH that contains, in an amino acid sequence of an FADGDH derived from the genus *Aspergillus*, an amino acid substitution at position 59 or at a position equivalent thereto, and that has an improved temperature dependency when compared to pre-modification.

Item C2. The modified FADGDH according to item C1, wherein the FADGDH is derived from *Aspergillus oryzae.*

Item C3. The modified FADGDH according to item C2, wherein the FADGDH derived from *Aspergillus oryzae* has an amino acid sequence shown in SEQ ID NO: 1 or SEQ ID NO: 2.

Item C4. The modified FADGDH according to any of items C1 to C3, wherein the amino acid substitution of the FADGDH derived from the genus *Aspergillus* is any of the substitutions selected from the group consisting of G59A, G59C, G59D, G59F, G59H, G59K, G59L, G59M, G59N, G59P, G59Q, G59S, G59T, G59W, and G59Y, or the modified FADGDH contains an equivalent amino acid substitution at a position equivalent thereto.

Item C5. The modified FADGDH according to item C4, wherein the amino acid sequence of the FADGDH derived from the genus *Aspergillus* contains an amino acid substitution at position 59 or at a position equivalent thereto, and the modified FADGDH has a reduced action to xylose when compared to pre-modification.

Item C6. The modified FADGDH according to item C5, wherein the amino acid substitution of the FADGDH derived from the genus *Aspergillus* is any of the substitutions selected from the group consisting of G59C, G59D, G59K, G59M, G59Q, G59S, and G59T, or the modified FADGDH contains an equivalent amino acid substitution at a position equivalent thereto.

Item C7. The modified FADGDH according to item C6, wherein the amino acid sequence of the FADGDH derived from the genus *Aspergillus* contains an amino acid substitution at position 59 or at a position equivalent thereto, and the modified FADGDH has an improved temperature dependency and a reduced action to xylose when compared to pre-modification.

Item D1. A protein set forth by any of the following (Da) to (Dc).

(Da) A protein that contains, in an amino acid sequence shown in SEQ ID NO: 1, a substitution of an amino acid at position 504 with another amino acid.

(Db) A protein that contains, in an amino acid sequence shown in SEQ ID NO: 2, a substitution of an amino acid at position 504 with another amino acid.

(Dc) A protein that contains, in an amino acid sequence that has a homology not lower than 60% with at least either SEQ ID NO: 1 or SEQ ID NO: 2 and that encodes a protein having a glucose dehydrogenase activity, a substitution of an amino acid at a position equivalent to position 504 of SEQ ID NO: 1 or to position 504 of SEQ ID NO: 2 with another amino acid.

Item D2. The protein according to item D1, wherein the protein has a glucose dehydrogenase activity and has an amino acid sequence in which one or more amino acids are additionally deleted, substituted, or added (inserted) at a position other than the position having the substitution of an amino acid.

Item D3. The protein according to item D1, wherein N at position 504 or an amino acid at a position equivalent thereto is substituted with G or S.

Item E1. A protein set forth by any of the following (Ea) to (Ec).

(Ea) A protein that contains, in an amino acid sequence shown in SEQ ID NO: 1, a substitution of an amino acid at either position 53 or position 60 with another amino acid.

(Eb) A protein that contains, in an amino acid sequence shown in SEQ ID NO: 2, a substitution of an amino acid at either position 53 or position 60 with another amino acid.

(Ec) A protein that contains, in an amino acid sequence that has a homology not lower than 60% with at least either SEQ ID NO: 1 or SEQ ID NO: 2 and that encodes a protein having a glucose dehydrogenase activity, a substitution of an amino acid at a position equivalent to either position 53 or position 60 in SEQ ID NO: 1, or to either position 53 or position 60 in SEQ ID NO: 2 with another amino acid.

Item E2. The protein according to item E1, wherein the protein has a glucose dehydrogenase activity and has an amino acid sequence in which one or more amino acids are additionally deleted, substituted, or added (inserted) at a position other than the position having the substitution of an amino acid.

Item E3. The protein according to item E1, wherein: G at position 53 or an amino acid at a position equivalent thereto is substituted with any of the amino acids selected from the group consisting of F, L, Q, R, S, W, and Y; or S at position 60 or an amino acid at a position equivalent thereto is substituted with any of the amino acids selected from the group consisting of C, D, G, L, N, T, and V.

Item F1. A polynucleotide encoding an amino acid sequence of the protein according to any of items A1 to A3, B1 to B6, C1 to C7, D1 to D3, and E1 to E3.

Item F2. A vector that contains the gene according to item F1.

Item F3. A transformant transformed using the vector according to item F2.

Item F4. A method for producing a protein having a glucose dehydrogenase activity, the method comprising culturing the transformant according to item F3, and collecting the protein having a glucose dehydrogenase activity.

Item F5. A glucose assay kit comprising the protein according to any of items A1 to A3, B1 to B6, C1 to C12, D1 to D3, and E1 to E3.

Item F6. A glucose sensor comprising the protein according to any of items A1 to A3, B1 to B6, C1 to 12, D1 to D3, and E1 to E3.

Item F7. A method for measuring glucose level in a sample, the method comprising causing the protein according to any of items A1 to A3, B1 to B6, C1 to 12, D1 to D3, and E1 to E3, to act on a sample that contains glucose.

Advantageous Effects of Invention

A protein of the present invention is a glucose dehydrogenase that has superior temperature dependency. More specifically, the protein of the present invention is a glucose dehydrogenase whose activity is less influenced by a change in temperature of a usage environment. Therefore, when the protein of the present invention is used, measurement of glucose level in a sample can be performed more accurately without being influenced by a change in temperature of a usage environment. Since enzyme activity of the protein of the present invention is less influenced by a change in temperature of a usage environment, the protein allows accurate measurement of glucose level in a sample even, for example, at a temperature lower or higher than an ordinary room temperature. Thus, the protein of the present invention is useful as an enzyme to be used in a clinical test reagent for measuring blood glucose level.

The protein of the present invention not only has a reduced temperature dependency but also has a reduced action to xylose. Therefore, the protein of the present invention is superior for measurement of blood glucose level also from the standpoint of substrate specificity.

A method of the present invention allows efficient production of the new protein that has the superior property as described above.

The present invention allows creation of a new FADGDH that has a high specific activity and that is useful as an enzyme to be used in a clinical test reagent, and allows industrial production of the FADGDH in large quantity.

BRIEF DESCRIPTION OF DRAWINGS

FIG. 1 shows a change in activity of an FADGDH that has an amino acid sequence shown in SEQ ID NO: 2, which is caused by a change in temperature.

FIG. 2: FIG. 2 is a comparison of an amino acid sequence of a wild-type FADGDH derived from *Aspergillus oryzae* (SEQ ID NO: 1), and an amino acid sequence of a wild-type FADGDH derived from *Aspergillus terreus* (SEQ ID NO: 3).

DESCRIPTION OF EMBODIMENTS

Figure 1:
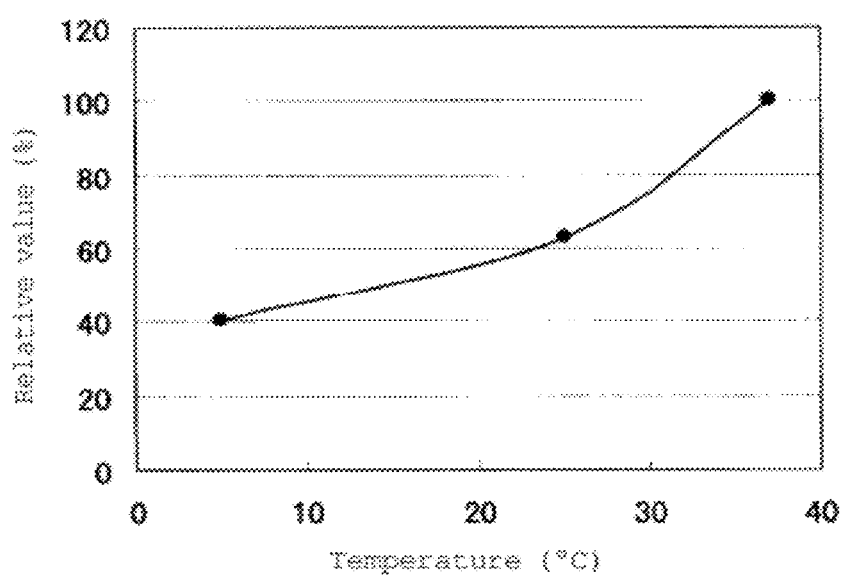
FIG. 1.

Details of the present invention are described in the following.

The present invention provides a protein of the following (A1) or (A2) (hereinafter, respectively represented as protein (A1) and protein (A2); and protein (A1) and protein (A2) are both represented as the protein of the present invention):

(A1) a protein having an amino acid sequence that contains, in an amino acid sequence shown in SEQ ID NO: 2, any of the amino acid substitutions set forth by the following (a):

(a) S60C, S60D, S60L, S60N, S60V, S60G, S60T, N504G, N504S, G59Y, G59F, G59M, G59T, G59C, G59L, G59H, G59K, G59Q, G59W, G59N, G59P, G59A, G59S, G59D, F58E, F58Q, F58S, F58T, F58A, F58I, F58M, F58Y, F58H, F58L, G53R, G53S, G53F, G53L, G53W, G53Y, and G53Q, (A2) a protein that satisfies the following (i) to (iii);

(i) one having an amino acid sequence that contains, in an amino acid sequence having at least 60% homology with the amino acid sequence shown in SEQ ID NO: 2, an amino acid set forth by the following (b), (b) 60C, 60D, 60L, 60N, 60V, 60G, 60T, 504G, 504S, 59Y, 59F, 59M, 59T, 59C, 59L, 59H, 59K, 59Q, 59W, 59N, 59P, 59A, 59S, 59D, 58E, 58Q, 58S, 58T, 58A, 58I, 58M, 58Y, 58H, 58L, 53R, 53S, 53F, 53L, 53W, 53Y, and 53Q, (ii) one having a glucose dehydrogenase activity, and (iii) one having an improved temperature dependency when compared to a protein that has the amino acid sequence of SEQ ID NO: 2.

When the amino acid sequence shown in SEQ ID NO: 2 is used as a reference, protein (A1) has a specific amino acid substitution at a specific position in the amino acid sequence shown in SEQ ID NO: 2. The specific amino acid substitution at the specific position is any of the substitutions shown in the following.

(a): S60C, S60D, S60L, S60N, S60V, S60G, S60T, N504G, N504S, G59Y, G59F, G59M, G59T, G59C, G59L, G59H, G59K, G59Q, G59W, G59N, G59P, G59A, G59S, G59D, F58E, F58Q, F58S, F58T, F58A, F58I, F58M, F58Y, F58H, F58L, G53R, G53S, G53F, G53L, G53W, G53Y, and G53Q.

As shown in later described examples, protein (A1) has an improved temperature dependency when compared to a temperature dependency of an FADGDH that has an amino acid sequence shown in SEQ ID NO: 2. The amino acid at the specific position is an amino acid at position 60, 504, 59, 58, or 53 in the amino acid sequence shown in SEQ ID NO: 2. Protein (A1) may have substitutions of amino acids at two or more of the specific positions as long as the temperature dependency of protein (A1) is improved.

In the context of the present invention, an amino acid included in an amino acid sequence is represented by a single alphabet or three alphabets. For example, glycine is represented as Gly or G. A position of an amino acid in an amino acid sequence is specified using a number. For example, a case where serine located at the 80-th is substituted with cysteine, is represented as "S80C." In addition, "80C" indicates that an amino acid at position 80 (or 80-th) is Cys(C) regardless of whether or not there is a mutation. For the representation of amino acids in SEQ ID NO: 1, SEQ ID NO: 2, and SEQ ID NO: 3, methionine is given the number 1.

In the context of the present invention, SEQ ID NO: 1 shows an amino acid sequence of a wild-type FADGDH derived from *Aspergillus oryzae*. SEQ ID NO: 2 shows an amino acid sequence obtained by substituting glycine at position 163 with arginine and substituting valine at position 551 with cysteine in the amino acid sequence of SEQ ID NO: 1. A protein comprising the amino acid sequence shown in SEQ ID NO: 2 has a glucose dehydrogenase activity. Hereinafter, the protein comprising the amino acid sequence shown in SEQ ID NO: 2 is represented as an FADGDH of SEQ ID NO: 2 as appropriate. The amino acid sequences of SEQ ID NOS: 1 and 2 are disclosed in, for example, Patent Literature 2 or Patent Literature 3. Specific activities of an FADGDH having the amino acid sequence of SEQ ID NO: 1 and the FADGDH having the amino acid sequence of SEQ ID NO: 2 are almost equal and are both about 600 U/A280.

Protein (A1) has the above described specific amino acid substitution in the amino acid sequence shown in SEQ ID NO: 2, and thereby has a property of an improved temperature dependency while retaining the glucose dehydrogenase activity.

Temperature Dependency

In the context of the present invention, a temperature dependency refers to a fluctuation characteristic of a protein's glucose dehydrogenase activity in association with a change in temperature of an environment in which the protein exists. An improvement in the temperature dependency refers to having a small change in enzyme activity associated with a change in the environmental temperature, and maintaining a more constant enzyme activity in a broad temperature range condition.

Whether a temperature dependency has improved is determined based on a temperature dependency of the FADGDH comprising the amino acid sequence shown in SEQ ID NO: 2, and, more specifically, is determined in accordance with the following (1) to (5).

(1) An activity value (U/ml) at 37° C. after 24 hours of processing is measured and is represented as A.

(2) An activity value (Urn') at 25° C. after 24 hours of processing is measured and is represented as B.

(3) When A is defined as 100%, a relative value (%) of B is calculated and is represented as C.

(4) When a value of C for the FADGDH of SEQ ID NO: 2 is defined as 1, a relative value of C for a modified protein such as protein (A1) or the like is obtained, and is represented as D.

(5) As shown in the following Example B1, when the enzyme activity of the FADGDH of SEQ ID NO: 2 at 37° C. is defined as 100%, the enzyme activity of that at 25° C. is 63%. Therefore, when the value of C for a modified protein is larger than 63%, the value of D becomes larger than 1. Thus, as the value of D of a modified FADGDH departs from 1 and approaches 1.59, the temperature dependency becomes low and improved.

Since the protein of the present invention has an Improved temperature dependency, the protein has a value of D that is at least larger than 1. The value of D is preferably not smaller than 1.05, more preferably not smaller than 1.1, further preferably not smaller than 1.15, still further preferably not smaller than 1.2, even further preferably not smaller than 1.25, and yet further preferably not smaller than 1.3.

The amino acid substitution included in the amino acid sequence of protein (A1) may be any of the substitutions listed in (a) above. From the standpoint of improving temperature dependency, the amino acid substitution is preferably any of S60C, S60D, S60L, S60N, S60V, N504G, N504S, G59Y, G59F, G59M, G59T, G59C, G59L, G59H, G59K, G59Q, G59W, G59N, G59P, G59A, G59S, F58E, F58Q, F58S, F58T, F58A, F58I, F58M, F58Y, G53R, G53S, G53F, G53L, G53W, G53Y, and G53Q. A modified FADGDH that has any of these amino acid substitutions has a value of D not smaller than 1.05.

More preferably, the amino acid substitution is any of S60C, S60D, S60L, N504G, N504S, G59Y, G59F, G59M, G59T, G59C, G59L, G59H, G59K, G59Q, G59W, G59N, F58E, F58Q, F58S, F58T, G53R, G53S, G53F, G53L, G53W, and G53Y. A modified FADGDH that has any of these amino acid substitutions has a value of D not smaller than 1.1.

Further preferably, the amino acid substitution is any of S60C, N504G, G59Y, G59F, G59M, G59T, G59C, G59L, F58E, and G53R. A modified FADGDH that has any of these amino acid substitutions has a value of D not smaller than 1.15.

Still further preferably, the amino acid substitution is any of S60C, N504G, G59Y, G59F, G59M, and G59T. A modified FADGDH that has any of these amino acid substitutions has a value of D not smaller than 1.2. Even further preferably, the amino acid substitution is either S60C or N504G. A modified FADGDH that has either of these amino acid substitutions has a value of D not smaller than 1.25. The most preferable amino acid substitution is S60C that provides a value of D not smaller than 1.3.

On the other hand, in addition to the improvement in temperature dependency, from a standpoint of having a reduced action to xylose (i.e., an improved substrate specificity), a preferable amino acid substitution is any of the substitutions selected from the group consisting of S60C, S60D, S60N, S60G, S60T, N504G, G59M, G59T, G59C, G59K, G59Q, G59W, G59D, F58E, F58Q, F58S, F58T, F58A, F58I, F58M, F58Y, F58H, F58L, G53R, G53S, G53F, G53L, G53W, G53Y, and G53Q. With regard to these amino acid substitutions, as long as the action to xylose is reduced and the temperature dependency is improved, two or more amino acid substitutions at different position may be included.

From a standpoint of further improving the temperature dependency and further reducing the action to xylose, a more preferable amino acid substitution is any of the substitutions selected from the group consisting of S60C, S60D, N504G, G59Y, G59M, G59T, G59C, G59K, G59Q, G59W, F58E, F58Q, F58S, F58T, G53R, G53S, G53F, G53L, G53W, and G53Y. Two or more of these amino acid substitutions may exist as long as the amino acids that are to be substituted are located at different positions.

Protein (A1) may have an additional mutation (substitution, addition, deletion, insertion of an amino acid) in the amino acid sequence as long as protein (A1) has a glucose dehydrogenase activity and has an improved temperature dependency. For example, protein (A1) may have amino acid substitutions at two or more different positions selected from the above described (a). Furthermore, an amino acid sequence obtained by substituting arginine at position 163 with glycine and substituting cysteine at position 551 with valine in the amino acid sequence of SEQ ID NO: 2, is the amino acid sequence (SEQ ID NO: 1) of the wild-type FADGDH. Therefore, in addition to the above specified amino acid substitutions, protein (A1) may have a substitution of the 163-th amino acid with glycine and a substitution of the 551-th amino acid with valine.

Protein (A2) satisfies the following requirements of (i) to (iii):

(i) one having an amino acid sequence that contains, in an amino acid sequence having at least 60% homology with the amino acid sequence shown in SEQ ID NO: 2, any of the amino acid set forth by the following (b), (b) 60C, 60D, 60L, 60N, 60V, 60G, 60T, 504G, 504S, 59Y, 59F, 59M, 59T, 59C, 59L, 59H, 59K, 59Q, 59W, 59N, 59P, 59A, 59S, 59D, 58E, 58Q, 58S, 58T, 58A, 58I, 58M, 58Y, 58H, 58L, 53R, 53S, 53F, 53L, 53W, 53Y, and 53Q, (ii) one having a glucose dehydrogenase activity, and (iii) one having an improved temperature dependency when compared to the protein having the amino acid sequence of SEQ ID NO: 2.

Thus, protein (A2) has an amino acid sequence that has an amino acid homology of at least 60% with the amino acid sequence shown in SEQ ID NO: 2, and includes at least one amino acid set forth by the above described (b). Furthermore, protein (A2) retains a glucose dehydrogenase activity and an improved temperature dependency when compared to the FADGDH of SEQ ID NO: 2.

The amino acid sequence that has a homology not lower than 60% with the amino acid sequence of SEQ ID NO: 2 and that encodes a protein having a glucose dehydrogenase activity include, for example, an amino acid sequence of a wild-type FADGDH derived from *Aspergillus terreus* shown in SEQ ID NO: 3. That amino acid sequence is disclosed in Patent Literature 5.

In the context of the present invention, a homology of amino acid sequences refers to a value obtained from a comparison using GENETYX software. For example, when a comparative analysis is performed on the amino acid sequence of the wild-type FADGDH derived from *Aspergillus oryzae* (SEQ ID NO: 1) and the amino acid sequence of the wild-type FADGDH derived from *Aspergillus terreus* (SEQ ID NO: 3) using the GENETYX software, the homology between the two is 63.5% (cf. FIG. 2). In addition, the homology between the amino acid sequence shown in SEQ ID NO: 2 and the amino acid sequence shown in SEQ ID NO: 3 is 63.4%.

The protein that has a glucose dehydrogenase activity and an improved temperature dependency, and that has an amino acid having a 60% homology with the amino acid sequence of SEQ ID NO: 2, can be produced by, for example, creating an alignment between SEQ ID NO: 3, and SEQ ID NO: 1 or SEQ ID NO: 2, and adding a mutation to a domain other than a preserved domain.

Domains that are estimated not to influence the enzyme activity and temperature dependency even when a mutation is added to the amino acid sequence, include domains located on a protein surface indicated from an X-ray crystal structure of the protein. Examples of those domains include positions 1 to 40, 111 to 190, 213 to 310, 340 to 397, 420 to 435, 455 to 492, 514 to 538, and 552 to 572.

The amino acid sequence of protein (A2) is not particularly limited as long as it satisfies the requirements of the above described (i) to (iii); however, the homology between the amino acid sequence of protein (A2) and the amino acid sequence shown in SEQ ID NO: 2 is preferably not smaller than 70%, more preferably not smaller than 80%, further preferably not smaller than 90%, and particularly preferably not smaller than 95%. It should be noted that an amino acid homology in the context of the present invention refers to an amino acid identity.

As a result of having any of the specific amino acids listed in the above described (b), protein (A2) has a temperature dependency that is superior to that of the FADGDH of SEQ ID NO: 2. Among the specific amino acids listed in the above described (b), a preferable amino acid is any of the amino acids selected from the group consisting of 60C, 60D, 60L, 60N, 60V, 504G, 504S, 59Y, 59F, 59M, 59T, 59C, 59L, 59H, 59K, 59Q, 59W, 59N, 59P, 59A, 59S, 58E, 58Q, 58S, 58T, 58A, 58I, 58M, 58Y, 53R, 53S, 53F, 53L, 53W, 53Y, and 53Q.

The specific amino acid is more preferably any of the amino acids selected from the group consisting of 60C, 60D, 60L, 504G, 504S, 59Y, 59F, 59M, 59T, 59C, 59L, 59H, 59K, 59Q, 59W, 59N, 58E, 58Q, 58S, 58T, 53R, 53S, 53F, 53L, 53W, and 53Y.

The specific amino acid is further preferably any of the amino acids selected from the group consisting of 60C, 504G, 59Y, 59F, 59M, 59T, 59C, 59L, 58E, and 53R.

The specific amino acid is still further preferably any of the amino acids selected from the group consisting of 60C, 504G, 59Y, 59F, 59M, and 59T, even further preferably is any of the amino acids selected from the group consisting of 60C and 504G, and the most preferable amino acid is 60C.

As long as protein (A2) has an improved temperature dependency, a plurality of the specific amino acids exemplified above may exist in different positions of the amino acid sequence.

In addition to the improvement in temperature dependency, from a standpoint of having a reduced action to xylose (i.e., an improved substrate specificity), a preferable amino acid is any of the amino acids selected from the group consisting of 60C, 60D, S60N, 60G, 60T, 504G, 59M, 59T, 59C, 59K, 59Q, 59W, 59D, 58E, 58Q, 58S, 58T, 58A, 58I, 58M, 58Y, 58H, 58L, 53R, 53S, 53F, 53L, 53W, 53Y, and 53Q. Two or more of these amino acids may exist as long as the amino acids are located at different positions.

From a standpoint of further improving the temperature dependency and further reducing the action to xylose, a more preferable amino acid substitution is any of the amino acid substitutions selected from the group consisting of 60C, 60D, 504G, 59Y, 59M, 59T, 59C, 59K, 59Q, 59W, 58E, 58Q, 58S, 58T, 53R, 53S, 53F, 53L, 53W, and 53Y. Two or more of these amino acid substitutions may exist as long as the amino acids that are to be substituted are located at different positions.

In the present invention, an action to xylose is represented as a relative ratio % (taking glucose as 100%) of a reaction rate obtained when xylose is used as a substrate, to a reaction rate obtained when glucose is used as a substrate. A value of an action to xylose for the FADGDH comprising the amino acid sequence shown in SEQ ID NO: 2 is defined as 1, and a relative ratio % of each modified enzyme is calculated. Therefore, it is determined that the action to xylose is reduced when this value is small.

The modified FADGDH of the present invention preferably has a value of D not smaller than 1.05, more preferably has a value of D not smaller than 1.1, further preferably has a value of D not smaller than 1.15, and even further preferably has a value of D not smaller than 1.2.

The modified FADGDH of the present invention preferably is a modified FADGDH whose ratio of action to xylose is reduced to not higher than 0.9 when compared to pre-modification; and, further preferably, is reduced to not higher than 0.8 when compared to pre-modification.

With regard to the method for measuring the temperature dependency and the action to xylose, a later described method for measuring FADGDH activity is used.

In another embodiment, the present invention provides a protein set forth in the following.

B: A modified FADGDH that contains, in the amino acid sequence of the FADGDH shown in SEQ ID NO: 1 or SEQ ID NO: 2, an amino acid substitution at position 58 or at a position equivalent thereto, and that has an improved temperature dependency when compared to pre-modification.

In addition, one embodiment of the present invention is a modified FADGDH that contains, in the above described protein, any of the amino acid substitutions selected from the group consisting of F58A, F58E, F58H, F58I, F58L, F58M, F58Q, F58S, F58T, and F58Y, or contains an equivalent amino acid substitution at a position equivalent thereto, and that has an improved temperature dependency.

In another embodiment, the present invention provides a protein set forth in the following.

C: A modified FADGDH that contains, in the amino acid sequence of the FADGDH shown in SEQ ID NO: 1 or SEQ ID NO: 2, an amino acid substitution at position 59 or at a position equivalent thereto, and that has an improved temperature dependency when compared to pre-modification.

In addition, one embodiment of the present invention is a modified FADGDH that contains, in the above described protein, any of the amino acid substitutions selected from the group consisting of G59A, G59C, G59D, G59F, G59H, G59K, G59L, G59M, G59N, G59P, G59Q, G59S, G59T, G59W, and G59Y, or contains an equivalent amino acid substitution at a position equivalent thereto, and that has an improved temperature dependency.

In another embodiment, the present invention provides a protein set forth by the following.

D: A protein represented by the following (a) to (c):
(a) a protein that contains, in an amino acid sequence shown in SEQ ID NO: 1, a substitution of an amino acid at position 504 with another amino acid;
(b) a protein that contains, in an amino acid sequence shown in SEQ ID NO: 2, a substitution of an amino acid at position 504 with another amino acid; and
(c) a protein that contains, in an amino acid sequence that has a homology not lower than 60% with at least either SEQ ID NO: 1 or SEQ ID NO: 2 and that encodes a protein having a glucose dehydrogenase activity, a substitution of an amino acid at a position equivalent to position 504 of SEQ ID NO: 1 or to position 504 of SEQ ID NO: 2 with another amino acid.

In addition, one embodiment of the present invention is a protein in which, in the above described protein, N at position 504 or an amino acid at a position equivalent thereto is substituted with G or S.

In another embodiment, the present invention provides a protein set forth in the following.

E: A protein represented by any of the following (a) to (c):
(a) a protein that contains, in an amino acid sequence shown in SEQ ID NO: 1, a substitution of an amino acid at either position 53 or position 60 with another amino acid;
(b) a protein that contains, in an amino acid sequence shown in SEQ ID NO: 2, a substitution of an amino acid at either position 53 or position 60 with another amino acid; and
(c) a protein that contains, in an amino acid sequence that has a homology not lower than 60% with at least either SEQ ID NO: 1 or SEQ ID NO: 2 and that encodes a protein having a glucose dehydrogenase activity, a substitution of an amino acid at a position equivalent to either position 53 or position 60 in SEQ ID NO: 1, or to either position 53 or position 60 in SEQ ID NO: 2 with another amino acid.

In addition, one embodiment of the present invention is a protein in which, in the above described protein, G at position 53 or an amino acid at a position equivalent thereto is substituted with any of the amino acids selected from the group consisting of F, L, Q, R, S, W, and Y, or S at position 60 or an amino acid at a position equivalent thereto is substituted with any of the amino acids selected from the group consisting of C, D, G, L, N, T, and V.

In the context of the present invention, a position in a certain amino acid sequence is determined to be a position equivalent to position 79 of SEQ ID NO: 1 when, for example, the position corresponds to position 79 of SEQ ID NO: 1 after comparing primary structures of sequences (e.g., alignment) using the GENETYX software. In addition, knowledge regarding three-dimensional conformations may be used as a reference if necessary.

For example, based on comparison data of an alignment between the amino acid sequence of the wild-type FADGDH derived from *Aspergillus oryzae* (SEQ ID NO: 1) and the amino acid sequence of the wild-type FADGDH derived from *Aspergillus terreus* (SEQ ID NO: 3), a position equivalent to position 55 in the amino acid sequence shown in SEQ ID NO: 2 corresponds to G at position 51 in the amino acid sequence of the wild-type FADGDH derived from *Aspergillus terreus*. Similarly, a position equivalent to position 60 in the amino acid sequence shown in SEQ ID NO: 2 corresponds to S at position 56 of the wild-type FADGDH derived from *Aspergillus terreus*. A position equivalent to position 446 in the amino acid sequence shown in SEQ ID NO: 2 corresponds to L at position 442 in the amino acid sequence of the wild-type FADGDH derived from *Aspergillus terreus*. An amino acid at position 412 of SEQ ID NO: 1 or SEQ ID NO: 2 corresponds to an amino acid at position 408 of SEQ ID NO: 3 (cf. FIG. 2).

As the GENETYX software, for example, GENETYX WIN Version 6.1 sold by GENETYX Corporation may be used.

The above described protein also includes a protein that has a glucose dehydrogenase activity and that has an amino acid sequence in which one or more amino acids are additionally deleted, substituted, or added (inserted) at a position other than the position having the substitution of an amino acid.

Modified FADGDH Having Reduced Action to Xylose

The present invention also provides a modified FADGDH that has a reduced action to xylose when compared to pre-modification.

In addition, one embodiment of the present invention is a modified FADGDH that contains, in the amino acid sequence of the FADGDH shown in SEQ ID NO: 1 or SEQ ID NO: 2, an amino acid substitution at position 58 or at a position equivalent thereto, and that has a reduced action to xylose when compared to pre-modification.

Furthermore, one embodiment of the present invention is a modified FADGDH that contains, in the amino acid sequence of the FADGDH shown in SEQ ID NO: 1 or SEQ ID NO: 2, an amino acid substitution at position 59 or at a position equivalent thereto, and that has a reduced action to xylose when compared to pre-modification.

In addition, one preferable embodiment of the present invention is a modified FADGDH that contains, in the above described protein, any of the amino acid substitutions selected from the group consisting of F58A, F58E, F58H, F58I, F58L, F58M, F58Q, F58S, F58T, and F58Y, or contains an equivalent amino acid substitution at a position equivalent thereto.

Furthermore, one preferable embodiment of the present invention is a modified FADGDH that contains, in the above described protein, any of the amino acid substitutions selected from the group consisting of G59C, G59D, G59K, G59M, G59Q, G59S, and G59T, or contains an equivalent amino acid substitution at a position equivalent thereto.

A protein that contains, in the above described protein, a substitution of N at position 504 or an amino acid at a position equivalent thereto with G, has a reduced action to xylose when compared to pre-modification.

A protein that contains, in the above described protein, a substitution of G at position 53 or an amino acid at a position equivalent thereto with any of the amino acids selected from the group consisting of F, L, Q, R, S, W, and Y, or a substitution of S at position 60 or an amino acid at a position equivalent thereto with any of C, D, G, and N, has a reduced action to xylose when compared to pre-modification.

Modified FADGDH Having Improved Temperature Dependency and Reduced Action to Xylose A protein of the present invention is a modified FADGDH that has an improved temperature dependency and a reduced action to xylose when compared to pre-modification.

In addition, one embodiment of the present invention is a modified FADGDH that contains, in the amino acid sequence of the FAD dependent glucose dehydrogenase (FADGDH) shown in SEQ ID NO: 1 or SEQ ID NO: 2, an amino acid substitution at position 58 or at a position equivalent thereto, and that has an improved temperature dependency and a reduced action to xylose when compared to pre-modification.

Furthermore, one embodiment of the present invention is a modified FADGDH that contains, in the amino acid sequence of the FADGDH shown in SEQ ID NO: 1 or SEQ ID NO: 2, an amino acid substitution at position 59 or a position equivalent thereto, and that has an improved temperature dependency and a reduced action to xylose when compared to pre-modification.

Still further, one embodiment of the present invention is a modified FADGDH that contains, in the protein having the amino acid sequence shown in SEQ ID NO: 1 or SEQ ID NO: 2, any of the amino acid substitutions selected from the group consisting of F58A, F58E, F58H, F58I, F58L, F58M, F58Q, F58S, F58T, and F58Y, or contains an equivalent amino acid substitution at a position equivalent thereto.

Even further, one embodiment of the present invention is a modified FADGDH that contains, in the protein having the amino acid sequence shown in SEQ ID NO: 1 or SEQ ID NO: 2, any of the amino acids substitution selected from the group consisting of G59C, G59D, G59K, G59M, G59Q, G59S, and G59T, or contains an equivalent amino acid substitution at a position equivalent thereto.

A protein that contains, in the protein having the amino acid sequence shown in SEQ ID NO: 1 or SEQ ID NO: 2, a substitution of N at position 504 or an amino acid at a position equivalent thereto with G, has an improved temperature dependency and a reduced action to xylose when compared to pre-modification.

A protein that contains, in the protein having the amino acid sequence shown in SEQ ID NO: 1 or SEQ ID NO: 2, a substitution of G at position 53 or an amino acid at a position equivalent thereto with any of the amino acids selected from the group consisting of F, L, Q, R, S, W, and Y, or a substitution of S at position 60 or an amino acid at a position equivalent thereto with any of the amino acids selected from the group consisting of C, D, G, and N, has an improved temperature dependency and a reduced action to xylose when compared to pre-modification.

The protein of the present embodiment may have amino acid substitutions at two or more positions selected from the group consisting of position 53 and position 60, as long as the protein has a glucose dehydrogenase activity and an improved temperature dependency and/or a reduced action to xylose when compared to pre-modification.

The protein of the present embodiment may have an amino acid substitution at one or more positions selected from the group consisting of position 53 and position 60, and may have an amino acid mutation at one or more positions (e.g., at several positions) other than those positions, as long as the protein has a glucose dehydrogenase activity, and has an improved temperature dependency and/or a reduced action to xylose when compared to pre-modification.

It should be noted that the above described positions that are converted may be an equivalent position in an amino acid sequence of a protein having an activity of an FADGDH derived from an origin (e.g., *Aspergillus terreus*) other than that (SEQ ID NO: 1) derived from *Aspergillus oryzae*, or that (SEQ ID NO: 2) obtained through a modification thereof. The equivalent position can be determined based on knowledge regarding a primary structure (e.g., alignment) or a three-dimensional conformation of the amino acid sequence. The alignment can be compared using GENETYX WIN (sold by GENETYX Corporation).

A gene of the present invention may include those obtained by changing its codon usage for the purpose of, for example, improving expression of GDH. Specifically, when substituting alanine at position 410 in SEQ ID NOS: 1 and 2 with valine, GCC located at 1228-th to 1230-th in a base sequence shown in SEQ ID NOS: 4 and 5 may be modified to be any of GTG, GTT, GTC, and GTA. When substituting phenylalanine at position 408 in SEQ ID NO: 3 with valine, TTT located at 1222-th to 1224-th in a base sequence shown in SEQ ID NO: 6 may be modified to be any of GTG, GTT, GTC, or GTA.

Method for Producing Protein of Present Invention

The protein of the present invention can be prepared using various publicly known means. Provided in the following is an example of a method for producing a modified FADGDH obtained by modifying the wild-type FADGDH derived from *Aspergillus oryzae* shown in SEQ ID NO: 1. Although there is no particular limitation in the production method, the production can be conducted with the steps set forth in the following.

As a technique for modifying the amino acid sequence forming the FAD dependent glucose dehydrogenase, a method commonly used for modifying genetic information can be employed. More specifically, DNA having genetic information of a modified protein is created, by converting a specific base or inserting or deleting a specific base of DNA having genetic information of a protein. Specific methods for converting base sequences in DNA include, for example, usage of a commercially available kit (Transformer Mutagenesis Kit: product of Clontech Laboratories, Inc., ExoIII/Mung Bean Deletion Kit: product of Stratagene Corp., Quick-Change Site Directed Mutagenesis Kit: product of Stratagene Corp., and the like), and utilization of polymerase chain reaction (PCR).

DNA having the genetic information of the modified. FAD dependent glucose dehydrogenase, which has been created, is ligated with a plasmid and introduced into a host microorganism to obtain a transformant that produces the modified FADGDH. As the plasmid used in such a case, for example, *Escherichia coli* JM109, *Escherichia coli* DH5a, *Escherichia coli* W3110, *Escherichia coli* C600, and the like can be used. For example, as a method for introducing a recombinant vector to a host microorganism when the host microorganism is a microorganism that belongs to *Escherichia coli*, a method of performing the introduction of recombinant DNA in presence of calcium ion can be employed. Furthermore, an electroporation method can also be used. In addition, a commercially available competent cell (e.g., Competent high JM109: product of Toyobo Co., Ltd.) can be used.

It should be noted that embodiments of the present invention also include a gene (polynucleotide) that encodes the modified FADGDH obtained by these processes, a vector containing the gene, and a transformant transformed with the vector.

Although a gene that becomes a basis of the modification for the modified FADGDH of the present invention is not particularly limited, the FADGDH derived from the genus *Aspergillus* is preferably used. Further preferably, the FADGDH derived from *Aspergillus oryzae* or *Aspergillus terreus* is used.

Examples of the FADGDH derived from *Aspergillus oryzae* include the protein shown in SEQ ID NO: 1 or SEQ ID NO: 2. Examples of the FADGDH derived from *Aspergillus terreus* include the protein shown in SEQ ID NO: 3.

One embodiment of the present invention is a gene (polynucleotide) that encodes any of the proteins described above.

With regard to a gene that encodes a pre-modified protein, a base sequence shown in SEQ ID NO: 4 is an example of a gene encoding the above described protein shown in SEQ ID NO: 1. In addition, a base sequence shown in SEQ ID NO: 5 is an example of a gene encoding the above described protein shown in SEQ ID NO: 2. Furthermore, a base sequence shown in SEQ ID NO: 6 is an example of a gene encoding the above described protein (FADGDH derived from *Aspergillus terreus*) shown in SEQ ID NO: 3.

For example, with regard to the gene (polynucleotide) of the present invention, a part that encodes an amino acid at position 58 or an amino acid at a position equivalent thereto in a sequence of a gene encoding a pre-modified protein described above, is substituted so as to encode another amino acid.

With regard to the gene (polynucleotide) of the present invention, a part that encodes an amino acid at position 59, position 82, or position 505, or an amino acid at a position equivalent thereto in a sequence of a gene encoding a pre-modified protein described above, is substituted so as to encode another amino acid.

With regard to the gene (polynucleotide) of the present invention, a part that encodes an amino acid at position 504 or an amino acid at a position equivalent thereto in a sequence of a gene encoding a pre-modified protein described above, is substituted so as to encode another amino acid.

With regard to the gene (polynucleotide) of present invention, a part that encodes an amino acid at either position 53 or position 60, or an amino acid at a position equivalent thereto in a sequence of a gene encoding a pre-modified protein described above, is substituted so as to encode another amino acid.

In another embodiment, the gene encoding the modified FADGDH of the present invention is DNA that encodes a protein having an FADGDH activity, and that hybridizes with DNA having a base sequence complementary to the base sequence shown in SEQ ID NO: 4, 5, or 6 under a stringent condition. Here, a stringent condition refers to a condition of hybridization in a temperature range between a Tm for highly homologous nucleic acids, e.g., a completely matched hybrid, and a temperature that is 15° C., preferably 10° C., below the Tm. Specifically, for example, this refers to a condition of hybridization at 68° C. for 20 hours in a commonly used hybridization buffer. In the present invention, a condition is considered stringent when it is for a base sequence encoding an amino acid sequence having a homology not lower than 50% with the amino acid sequence coded by the base sequence shown in SEQ ID NO: 4, 5, or 6; preferably not lower than 80%, further preferably not lower than 90%, and even further preferably not lower than 95%.

The gene of the present invention may include those obtained by changing its codon usage for the purpose of, for example, improving the expression of the GDH.

Embodiments of the present invention include: a vector containing the above described gene, a transformant transformed with the vector, and a method for producing a protein that has a glucose dehydrogenase activity by culturing the transformant and collecting the protein having a glucose dehydrogenase activity.

For example, the above described GDH gene is inserted in an expression vector (many thereof are known in the art, including plasmids), and an appropriate host (many thereof such as *Escherichia coli* are known in the art) is transformed using the expression vector. An obtained transformant is cultured, and microbial cells are collected from the culture medium by centrifugal separation. Then, the microbial cells are disrupted by a mechanical method or a method using an enzyme such as lysozyme, and, if necessary, a surfactant, a chelating agent such as EDTA, and the like are added for solubilization. As a result, a water soluble fraction containing the GDH can be obtained. Alternatively, the expressed GDH can be directly secreted in the culture medium with a use of an appropriate host-vector system.

A GDH containing solution obtained as described above can be precipitated by, for example, vacuum concentration, membrane concentration, a salting-out process using ammonium sulfate, sodium sulfate, or the like, a fractional precipitation method using a hydrophilic organic solvent such as methanol, ethanol, acetone, and the like. In addition, heat treatment and isoelectric focusing are also effective purification means. A purified GDH can be obtained by performing gel filtration using an adsorbent or a gel filtering agent, adsorption chromatography, ion exchange chromatography, or affinity chromatography. The purified enzyme preparation is preferably purified to a degree that results in a single band when electrophoresis (SDS-PAGE) is performed using the preparation.

These techniques can be performed in accordance with, for example, the following literature.

(a) Tanpakushitsu Jikken Protocol, Vol. 1 Functional Analysis, Vol. 2 Structural Analysis, (Shujunsha) edited by Yoshifumi Nishimura and Shigeo Ohno.

(b) Revised Tanpakushitsu Jikken Note, Extraction and Separation/Purification, (Yodosha) edited by Masato Okada and Kaori Miyazaki.

(c) Tanpakushitsu Jikken no Susumekata, (Yodosha) edited by Masato Okada and Kaori Miyazaki.

Alternatively, the techniques can be performed by the methods exemplified below.

The created DNA having genetic information of the protein is ligated to a vector, and introduced into a host microorganism.

Suitable vectors include those constructed for the purpose of genetic transformation from a phage or a plasmid capable of self-replicating in a host microorganism. For example, when *Escherichia coli* is used as the host microorganism, examples of the phage include Lambda gt10, Lambda gt11, and the like. For example, when *Escherichia coli* is used as the host microorganism, examples of the plasmid include pBR322, pUC19, pKK223-3, pBluescript, and the like. In particular, pBluescript and the like carrying a promoter capable of being recognized in *Escherichia coli* upstream of a cloning site are preferable.

The suitable host microorganism is not particularly limited as long as the host microorganism allows a recombinant vector to self-replicate, be stable, and to express a character of a foreign gene. *Escherichia coli* that can be used includes *Escherichia coli* W3110, *Escherichia coli* C600, *Escherichia coli* HB101, *Escherichia coli* J14109, and *Escherichia coli* DH5a.

As the method for introducing a recombinant vector to a host microorganism, for example, when the host microorganism is a microorganism that belongs to the genus *Escherichia*, a method of introducing a recombinant DNA in the presence of calcium ion can be employed. Furthermore, an electroporation method can be employed. Still Further, a commercially available competent cell (e.g., Competent High DH5a; product of Toyobo Co., Ltd.) can be employed. When yeast is used as the host, a lithium method or an electroporation method is employed. When Filamentous fungi are used, a protoplast method is employed.

In the present invention, the method for obtaining the gene encoding GDH includes the following methods. A predicted GDH gene can be found using genome sequence information of *Aspergillus oryzae*. Then, mRNA is prepared from microbial cells of *Aspergillus oryzae* and cDNA is synthesized therefrom. The cDNA obtained in a manner described above is used as a template for amplifying the GDH gene using PCR. Blunt ends or sticky ends of both DNAs of the obtained gene and the vector are ligated and closed using DNA ligase or the like to construct a recombinant vector. The recombinant vector is introduced into the host microorganism that allows the recombinant vector to replicate, and then a recombinant microorganism containing the gene encoding the GDH is obtained by using a marker for the vector.

The so-obtained microorganism which is the transformant is cultured in a nutrient medium for allowing GDH to be stably produced in large quantities. The transformant can be selected by searching for a microorganism that simultaneously expresses a marker for the vector and a GDH activity. For example, a microorganism that grows in a selection medium based on a drug resistance marker and that also produces GDH may be selected.

The base sequence of the GDH gene was sequenced by the dideoxy method described in Science, 214: 1205 (1981). Furthermore, the amino acid sequence of the GDH was estimated from the base sequence determined as described above.

Transferring the GDH gene from the recombinant vector which has been selected once as described above to a recombinant vector capable of replicating in another microorganism can be conducted easily by recovering the DNA for the GDH gene from the recombinant vector carrying the GDH gene using a restriction enzyme or PCR, and ligating the recovered DNA with a fragment of another vector. Transformation of other microorganisms with such vectors can be performed using a competent cell method that utilizes calcium treatment, an electroporation method, a protoplast method, and the like.

As long as the GDH gene of the present invention has a glucose dehydrogenase activity, the GDH gene may have a DNA sequence resulting in a deletion or substitution in some of the amino acid residues in the amino acid sequence obtained by translating the gene, or a DNA sequence resulting in an addition of or a substitution to other amino acid residues.

As the method for modifying the gene encoding the wild-type GDH, a technique commonly performed for modifying genetic information may be used. More specifically, DNA having genetic information of the modified protein is created, by converting a specific base, or inserting or deleting a specific base in DNA having genetic information of a protein. The specific methods for converting a base in DNA include, for example, usage of a commercially available kit (TransformerMutagenesis Kit: product of Clontech Laboratories, Inc., ExoIII/Mung Bean Deletion Kit: product of Stratagene Corp., QuickChange Site Directed Mutagenesis Kit: product of Stratagene Corp., and the like), and utilization of polymerase chain reaction (PCR).

With regard to the mode for culturing the host microorganism that is the transformant, a culturing condition may be selected in consideration of nutritional physiology nature of the host. The culturing is performed in a liquid in many cases, and, industrially, it is advantageous to perform the culturing with aeration and stirring. However, when considering the productivity, there are cases where it is advantageous to use a Filamentous fungus as a host and conduct solid culturing.

As a source of nutrient for the medium, those commonly used for culturing microorganisms may be widely used. As a carbon source, a carbon compound capable of being assimilated may be used, and, for example, glucose, sucrose, lactose, maltose, molasses, and pyruvic acid are used. Furthermore, as a nitrogen source, any applicable nitrogen compound may be used, and, for example, peptone, meat extract, yeast extract, casein hydrolysate, and alkaline extract of soybean meal are used. In addition, phosphates, carbonates, sulfates, salts of magnesium, calcium, potassium, iron, manganese, and zinc, specific amino acids, specific vitamins, and the like are used in accordance with needs.

Although the culturing temperature can be changed appropriately in a range in which the microbe grows and produces the GDH, preferably, the culturing temperature is about 20 to 37° C. The culturing time differs to some degree depending on the condition, and the culture may be completed at an appropriate time by judging the right timing at which the yield of the GDH becomes the highest. Typically, the culturing time is about 6 to 48 hours. Although the pH of the medium can be changed appropriately in a range in which the microbe grows and produces the GDH, preferably, the pH is in a range of about 6.0 to 9.0.

The culture medium that contains microbial cells producing the GDH in the culture can be directly collected and used. However, when the GDH exists in the culture medium, generally, in accordance with a method commonly used in the art, the GDH is utilized after separating a GDH containing solution and the microbial cells by filtration or centrifugal separation. When the GDH exists within the microbial cells, the microbial cells are collected from the obtained culture by means of filtration or centrifugal separation. Then, the collected microbial cells are disrupted by a mechanical method or a method using an enzyme such as lysozyme, and, if necessary, a surfactant and a chelating agent such as EDTA or the like are added to solubilize, isolate, and collect the GDH as a solution.

The GDH containing solution obtained as described above can be precipitated by, for example, vacuum concentration, membrane concentration, a salting-out process using ammonium sulfate, sodium sulfate, or the like, a fractional precipitation method using a hydrophilic organic solvent such as methanol, ethanol, acetone, and the like. In addition, heat treatment and isoelectric focusing are also effective purification means. Then, a purified GDH can be obtained by performing gel filtration using an adsorbent or a gel filtering agent, adsorption chromatography, ion exchange chromatography, or affinity chromatography.

For example, a purified enzyme preparation can be obtained through separation and purification by gel filtration using Sephadex gel (product of GE Healthcare Bioscience Corp.), or column chromatography using DEAE Sepharose CL-6B (product of GE Healthcare Bioscience Corp.), Octyl Sepharose CL-6B (product of GE Healthcare Bioscience Corp.), and the like. The purified enzyme preparation is preferably purified to a degree that results in a single band when electrophoresis (SDS-PAGE) is performed using the preparation.

In the present invention, glucose dehydrogenase activity of a protein is measured using the following conditions.

EXPERIMENTAL EXAMPLE

Reagents
50 mM PIPES buffer pH 6.5 (containing 0.1% Triton X-100)
24 mM PMS solution
2.0 mM 2,6-dichlorophenolindophenol (DCPIP) solution
1 M D-glucose solution A reaction reagent is obtained by mixing 20.5 ml of the PIPES buffer, 1.0 ml of the DCPIP solution, 2.0 ml of the PMS solution, and 5.9 ml of the D-glucose solution, which are described above.

Measuring Condition 3 ml of the reaction reagent is preheated at 37° C. for 5 minutes. 0.1 ml of a GDH solution is added thereto, the mixture is gently mixed. Then the mixture is placed in a spectrophotometer controlled at 37° C., and a change in absorbance at 600 nm is recorded for 5 minutes. From a linear portion of the record, a per-minute absorbance change ($\Delta OD_{TEST}$) is measured using water as a control. As a blank test, a per-minute absorbance change ($\Delta OD_{BLANK}$) is measured in a similar manner but by adding, to the reagent mixture, a solvent used for dissolving the GDH instead of the GDH solution. A GDH activity is obtained from the following formula using these values. Here, 1 unit (U) of the GDH activity is defined as an amount of enzyme that reduces 1 μmol of DCPIP in 1 minute in the presence of D-glucose at a concentration of 200 mM. When measuring an activity value at 25° C., measurement is performed by changing the temperature to 25° C. for the above described operation for 37° C. When measuring reactivity to xylose, 1 M D-xylose can be used instead of the above described 1 M D-glucose solution.

Activity(U/ml)={-(ΔODTEST-ΔODBLANK)×3.0× dilution factor}/{16.3×0.1×1.0}

It should be noted that, in the formula, 3.0 is a liquid amount (ml) of reaction reagent+enzyme solution, and 16.3 is a millimolar molecular absorbance coefficient ($cm^2/\mu mol$) for the present activity measurement condition, 0.1 is a liquid amount (ml) of the enzyme solution, and 1.0 is a length (cm) of a light path in a cell.

The specific activity of the FADGDH in the present invention is obtained in accordance with the following calculation formula.

Specific Activity(U/$A$280)=(Activity)/(Protein Concentration)

Here, protein concentration can be obtained by measuring absorbance at 280 nm using a molecule absorption photometer. Furthermore, A280 is an absorbance value at a wavelength of 280 nm.

When absorbance A280 at 280 nm is used, protein concentration <Protein> can be derived as:

<Protein>=$A$280/ε $M$(mol/$dm^3$).

Here, the molar absorbance coefficient εM of a protein at 280 nm can be obtained as:

ε$M$=Trp×5500+Tyr×1490+Cystine×125.

Glucose Assay Kit

Another feature of the present invention is a glucose assay kit including the modified FADGDH according to the present invention. The glucose assay kit of the present invention includes the modified FADGDH according to the present invention by an amount sufficient for at least one assay. Typically, the kit includes, in addition to the modified FADGDH of the present invention, a buffer and mediator necessary for the assay, a glucose standard solution for drawing a calibration curve, and a usage instruction. The modified FADGDH according to the present invention can be provided in various modes such as a lyophilized reagent or a solution in an appropriate preservation solution.

Glucose Sensor

Another feature of the present invention is a glucose sensor utilizing the modified FADGDH according to the present invention. As an electrode, a carbon electrode, a gold electrode, a platinum electrode, and the like are used. The enzyme of the present invention is immobilized on this electrode. Immobilization methods that can be used include: a method using a cross-linking reagent; a method of sealing using a polymer matrix; a method of covering using a dialysis membrane, a photocrosslinkable polymer, a conductive polymer, a redox polymer, or the like; immobilizing in a polymer or adsorbing-immobilizing onto the electrode, together with an electronic mediator represented by ferrocene or a derivative thereof; or a combination of those described above. Representatively, the modified FADGDH of the present invention is immobilized onto a carbon electrode using glutaraldehyde, and then, glutaraldehyde is blocked by a treatment using a reagent containing an amine group.

Measurement of glucose levels can be performed in the following manner. The buffer is poured in a constant temperature cell and maintained at a constant temperature. Potassium ferricyanide, phenazine methosulfate, and the like can be used as the mediator. An electrode having the modified FADGDH of the present invention immobilized thereto is used as a working electrode, and a counter electrode (e.g., platinum electrode) and a reference electrode (e.g., Ag/AgCl electrode) are used. A constant voltage is applied on the carbon electrode, and after the current stabilizes, a sample containing glucose is added and an increase in the current is measured. A glucose level in the sample can be calculated in accordance with a calibration curve drawn using glucose solutions with standard concentrations.

EXAMPLES

The present invention is described more specifically in the following with reference to Examples.

Example B1

Evaluation of Temperature Dependency of FADGDH

The FADGDH comprising the amino acid sequence shown in SEQ ID NO: 2 was used. An FADGDH purified preparation was prepared using the above described methods, and an activity thereof was measured in a 38 mM PIPES buffer (pH 6.5) at a predetermined temperature condition. A temperature dependency curve of the enzyme activity is shown in FIG. 1. The vertical axis represents a relative activity value at each temperature, wherein an activity value at 37° C. was defined as 100%. When the activity value at 37° C. was 100%, the activity value at 25° C. was about 63%, and the activity value at 5° C. was about 40%. Furthermore, the temperature dependency of the FADGDH of SEQ ID NO: 1 was similar to that of the FADGDH of SEQ ID NO: 2.

Example B2

Creating Modified FADGDH Gene

A commercially available *Escherichia coli* competent cell (*E. coli* DH5α; product of Toyobo Co., Ltd.) was transformed using a recombinant plasmid pAOGDH-M76 that contains the gene (SEQ ID NO: 5) encoding the FADGDH. Transformed cells were applied on an agar medium (1% polypeptone, 0.5% yeast extract, 0.5% NaCl, 1.5% agar; pH 7.3) containing ampicillin, and cultured overnight at 30° C. The obtained transformant was inoculated to a liquid medium (1% polypeptone, 0.5% yeast extract, 0.5% NaCl; pH 7.3) containing ampicillin (50 mg/ml; product of Nacalai Tesque, Inc.), and cultured overnight at 30° C. by shaking. A plasmid was prepared from the obtained microbial cells using a method commonly used in the art.

Using the plasmid as a template, a modified FADGDH was created using a synthetic oligonucleotide of SEQ ID NO: 8 designed such that phenylalanine at position 58 is substituted with alanine, and a synthetic oligonucleotide complementary thereto, in QuikChange™ Site-Directed Mutagenesis Kit (product of Stratagene Corp.).

Example B3

Preparation of Plasmid with Alanine-Modified FADGDH

A commercially available *Escherichia coli* competent cell (*E. coli* DH5a; product of Toyobo Co., Ltd.) was transformed using the obtained modified FADGDH, and cultured for 16 hours at 37° C. in an LB agar medium containing ampicillin. Then, a single colony of the modified FADGDH was inoculated to an LB liquid medium containing ampicillin, and cultured overnight at 30° C. by shaking. A plasmid was extracted from the obtained microbial cells using a method commonly used in the art. Relevant positions in the extracted plasmid were identified using a DNA sequencer (ABI Prism™ 3700 DNA Analyzer; product of Perkin-Elmer Inc.), and the modified FADGDH having a substitution with alanine was obtained. The plasmid in which phenylalanine at position 58 was substituted with alanine was named pAOGDH-M76-F58A.

Example B4

Preparation of Crude Enzyme Liquid Containing Modified FADGDH, and Comparison of Temperature Dependencies and Actions to Xylose A commercially available *Escherichia coli* competent cell (*E. coli* DH5a; product of Toyobo Co., Ltd.) was transformed using pAOGDH-M76-F58A obtained in Example B3, and cultured for 16 hours at 37° C. in an LB agar medium containing ampicillin. Then, a single colony of the alanine-modified FADGDH was inoculated to an LB liquid medium containing ampicillin, and cultured overnight at 30° C. by shaking. Microbial cells obtained from one portion of the culture medium using centrifugal separation were collected, and the microbial cells were homogenized in 50 mM phosphate buffer (pH 6.0) using glass beads to prepare a crude enzyme liquid.

By using the prepared crude enzyme liquid, GDH activity was measured at 25° C. and 37° C. using the above described activity measuring method. The results are shown in Table 1.

Table 1 shows the results of comparison of temperature dependency of F58A when culturing was performed for 24 hours at 30° C. in a 5 ml LB medium/test tube.

Comparing the modified sites and temperature dependencies, an advantageous effect was confirmed that substituting position 58 had improved temperature dependency when compared to the pre-modified FADGDH (described as Mut1), and thereby, position 58 was used as a candidate.

TABLE 1

Comparison of temperature dependency of modified FADGDH

| Variant | Temperature dependency (%) | Temperature dependency ratio (taking Mut1 as 1) |
| --- | --- | --- |
| Mut1 | 63.37 | 1.00 |
| F58A | 70.59 | 1.11 |

Example B5

Optimization of Amino Acid at Position 58

Using pAOGDH-M76 used in Example B2 as a template, modified FADGDHs were created using synthetic oligonucleotides of SEQ ID NO: 10 designed such that phenylalanine at position 58 is substituted with other types of amino acids and synthetic oligonucleotides complementary thereto, in QuikChange™ Site-Directed Mutagenesis Kit (product of Stratagene Corp.). A commercially available *Escherichia coli* competent cell (*E. coli* DH5a; product of Toyobo Co., Ltd.) was transformed using the modified FADGDH, and cultured for 16 hours at 37° C. in an LB agar medium containing ampicillin. Then, a single colony having the modified FADGDH was inoculated to an LB liquid medium containing ampicillin, and cultured overnight at 30° C. by shaking. Next, 1 ml of the culture medium was taken and a plasmid was extracted using a method commonly used in the art. Relevant positions in the extracted plasmid were identified using a DNA sequencer (ABI Prism™ 3700 DNA Analyzer; product of Perkin-Elmer Inc.). A plasmid containing a modified FADGDH having a substitution at position 58 to A was named pAOGDH-M76-F58A; a plasmid containing a modified FADGDH having a substitution at position 58 to C was named pAOGDH-M76-F58C; a plasmid containing a modified FADGDH having a substitution at position 58 to D was named pAOGDH-M76-F58D; a plasmid containing a modified FADGDH having a substitution at position 58 to E was named pAOGDH-M76-F58E; a plasmid containing a modified FADGDH having a substitution at position 58 to G was named pAOGDH-M76-F58G; a plasmid containing a modified FADGDH having a substitution at position 58 to H was named pAOGDH-M76-F58H; a plasmid containing a modified FADGDH having a substitution at position 58 to I was named pAOGDH-M76-F58I; a plasmid containing a modified FADGDH having a substitution at position 58 to K was named pAOGDH-M76-F58K; a plasmid containing a modified FADGDH having a substitution at position 58 to L was named pAOGDH-M76-F58L; a plasmid containing a modified FADGDH having a substitution at position 58 to M was named pAOGDH-M76-F58M; a plasmid containing a modified FADGDH having a substitution at position 58 to N was named pAOGDH-M76-F58N; a plasmid containing a modified FADGDH having a substitution at position 58 to P was named pAOGDH-M76-F58P; a plasmid containing a modified FADGDH having a substitution at position 58 to Q was named pAOGDH-M76-F58Q; a plasmid containing a modified FADGDH having a substitution at position 58 to R was named pAOGDH-M76-F58R; a plasmid containing a modified FADGDH having a substitution at position 58 to S was named pAOGDH-M76-F58S; a plasmid containing a modified FADGDH having a substitution at position 58 to T was named pAOGDH-M76-F58T; a plasmid containing a modified FADGDH having a substitution at position 58 to V was named pAOGDH-M76-F58V; a plasmid containing a modified FADGDH having a substitution at position 58 to W was named pAOGDH-M76-F58W; and a plasmid containing a modified FADGDH having a substitution at position 58 to Y was named pAOGDH-M76-F58Y.

Example B6

Comparison of Temperature Dependencies and Actions to Xylose of Modified FADGDHs Having Optimized Amino Acids at Position 58

A commercially available *Escherichia coli* competent cell (*E. coli* DH5a; product of Toyobo Co., Ltd.) was transformed using each of the plasmid obtained in Example B5, and cultured for 24 hours at 30° C. in an LB agar medium containing ampicillin. Then, crude enzyme solutions were prepared in a manner similar to Example B4, and their temperature dependencies were measured. The results of the temperature dependencies for the modified FADGDHs are shown in Table 2.

Table 2 shows the results of comparison of temperature dependencies and substrate specificities of the modified FADGDHs having a modification at position F58 when culturing was performed for 24 hours at 30° C. in 5 ml LB medium/test tubes. Temperature dependency was improved when compared to the pre-modified FADGDH, in the modified FADGDH having a substitution at position 58 to A, the modified FADGDH having a substitution at position 58 to E, the modified FADGDH having a substitution at position 58 to H, the modified FADGDH having a substitution at position 58 to I, the modified FADGDH having a substitution at position 58 to L, the modified FADGDH having a substitution at position 58 to M, the modified FADGDH having a substitution at position 58 to Q, the modified FADGDH having a substitution at position 58 to S, the modified FADGDH having a substitution at position 58 to T, and in the modified FADGDH having a substitution at position 58 to Y. Furthermore, actions to xylose were reduced in all the modified FADGDHs whose temperature dependencies were improved.

TABLE 2

Comparison of temperature dependencies and actions to xylose of the modified FADGDHs in which F58 is substituted with 19 types of amino acids

| Variant | Temperature dependency (%) | Temperature dependency ratio (taking Mut1 as 1) | Action to xylose (%) | Ratio of action to xylose (taking Mut1 as 1) |
|---|---|---|---|---|
| Mut1 | 63.70 | 1.00 | 10.50 | 1.00 |
| D | inactivated | — | inactivated | — |
| E | 74.24 | 1.17 | 8.77 | 0.84 |
| H | 66.34 | 1.04 | 7.35 | 0.70 |
| K | inactivated | — | inactivated | — |
| R | inactivated | — | inactivated | — |
| C | 57.63 | 0.90 | 13.14 | 1.25 |
| G | inactivated | — | inactivated | — |
| N | inactivated | — | inactivated | — |
| Q | 72.85 | 1.14 | 7.97 | 0.76 |
| S | 71.40 | 1.12 | 8.92 | 0.85 |
| T | 69.98 | 1.10 | 8.91 | 0.85 |
| Y | 67.25 | 1.06 | 7.56 | 0.72 |
| A | 69.46 | 1.09 | 8.57 | 0.82 |
| I | 69.01 | 1.08 | 8.65 | 0.82 |
| L | 65.99 | 1.04 | 9.82 | 0.94 |
| M | 69.12 | 1.08 | 8.58 | 0.82 |
| P | inactivated | — | inactivated | — |
| V | inactivated | — | inactivated | — |
| W | inactivated | — | inactivated | — |

Example C1

Creating Modified FADGDH Gene

A commercially available *Escherichia coli* competent cell (*E. coli* DH5a; product of Toyobo Co., Ltd.) was transformed using a recombinant plasmid pAOGDH-M76 that contains the gene (SEQ ID NO: 5) encoding the FADGDH. Transformed cells were applied on an agar medium (1% polypeptone, 0.5% yeast extract, 0.5% NaCl, 1.5% agar; pH 7.3) containing ampicillin, and cultured overnight at 30° C. The obtained transformant was inoculated to a liquid medium (1% polypeptone, 0.5% yeast extract, 0.5% NaCl; pH 7.3) containing ampicillin (50 mg/ml; Nacalai Tesque, Inc.), and cultured overnight at 30° C. by shaking. A plasmid was prepared from the obtained microbial cells using a method commonly used in the art.

Using the plasmid as a template, a modified FADGDH was created using a synthetic oligonucleotide of SEQ ID NO: 11 designed such that glycine at position 59 is substituted with alanine and a synthetic oligonucleotide complementary thereto, in QuikChange™ Site-Directed Mutagenesis Kit (product of Stratagene Corp.).

Example C2

Preparation of Plasmid with Alanine-Modified FADGDH

A commercially available *Escherichia coli* competent cell (*E. coli* DH5a; product of Toyobo Co., Ltd.) was transformed using the obtained modified FADGDH, and cultured for 16 hours at 37° C. in an LB agar medium containing ampicillin. Then, a single colony of the modified FADGDH was inoculated to an LB liquid medium containing ampicillin, and cultured overnight at 30° C. by shaking. A plasmid was extracted from the obtained microbial cells using a method commonly used in the art. Relevant positions in the extracted plasmid were identified using a DNA sequencer (ABI Prism™ 3700 DNA Analyzer; product of Perkin-Elmer Inc.), and the modified FADGDH having a substitution with alanine was obtained. The plasmid in which glycine at position 59 was substituted with alanine was named pAOGDH-M76-G59A.

Example C3

Preparation of Crude Enzyme Liquid Containing Modified FADGDH, and Comparison of Temperature Dependencies and Actions to Xylose A commercially available *Escherichia coli* competent cell (*E. coli* DH5a; product of Toyobo Co., Ltd.) was transformed using pAOGDH-M76-G59A obtained in Example C2, and cultured for 16 hours at 37° C. in an LB agar medium containing ampicillin. Then, a single colony of the alanine-modified FADGDH was inoculated to an LB liquid medium containing ampicillin, and cultured overnight at 30° C. by shaking. Microbial cells obtained from one portion of the culture medium using centrifugal separation were collected, and the microbial cells were homogenized in 50 mM phosphate buffer (pH 6.0) using glass beads to prepare a crude enzyme liquid.

By using the prepared crude enzyme liquid, GDH activity at 25° C. and 37° C., and action to xylose at 37° C. were measured using the above described activity measuring method. The results are shown in Table 3.

Table 3 shows the results of comparison of temperature dependency of G59A when culturing was performed for 24 hours at 30° C. in a 5 ml LB medium/test tube. Comparing the modified sites and temperature dependencies, an advantageous effect was confirmed that substituting the amino acid at position 59 with alanine had improved temperature dependency when compared to the pre-modified FADGDH, and thereby, position 59 was used as a candidate.

TABLE 3

Comparison of temperature dependency of modified FADGDH

| Variant | Temperature dependency (%) | Temperature dependency ratio (taking Mut1 as 1) |
|---|---|---|
| Mut1 | 62.55 | 100.00 |
| G59A | 66.46 | 106.25 |

Example C4

Optimization of Amino Acid at Position 59

Using pAOGDH-M76 used in Example C1 as a template, modified FADGDHs were created using synthetic oligonucleotides of SEQ ID NO: 15 designed such that tyrosine at position 59 is substituted with the 19 other types of amino acids and synthetic oligonucleotides complementary thereto, in QuikChange™ Site-Directed Mutagenesis Kit (product of Stratagene Corp.). A commercially available *Escherichia coli* competent cell (*E. coli* DH5a; product of Toyobo Co., Ltd.) was transformed using the modified FADGDH, and cultured for 16 hours at 37° C. in an LB agar medium containing ampicillin. Then, a single colony having the modified FADGDH was inoculated to an LB liquid medium containing ampicillin, and cultured overnight at 30° C. by shaking. Next, 1 ml of the culture medium was taken and a plasmid was extracted using a method commonly used in the art. Relevant positions in the extracted plasmid were identified using a DNA sequencer (ABI Prism™ 3700 DNA Analyzer; product of Perkin-Elmer Inc.). A plasmid containing a modified FADGDHRR having a substitution at position 59 to A was named pAOGDH-M76-G59A; a plasmid containing a modified FADGDHRR having a substitution at position 59 to C was named pAOGDH-M76-G59C; a plasmid containing a modified FADGDHRR having a substitution at position 59 to D was named pAOGDH-M76-G59D; a plasmid containing a modified FADGDHRR having a substitution at position 59 to E was named pAOGDH-M76-G59E; a plasmid containing a modified FADGDHRR having a substitution at position 59 to G was named pAOGDH-M76-G59G; a plasmid containing a modified FADGDHRR having a substitution at position 59 to H was named pAOGDH-M76-G59H; a plasmid containing a modified FADGDHRR having a substitution at position 59 to I was named pAOGDH-M76-G59I; a plasmid containing a modified FADGDHRR having a substitution at position 59 to K was named pAOGDH-M76-G59K; a plasmid containing a modified FADGDHRR having a substitution at position 59 to L was named pAOGDH-M76-G59L; a plasmid containing a modified FADGDHRR having a substitution at position 59 to M was named pAOGDH-M76-G59M; a plasmid containing a modified FADGDHRR having a substitution at position 59 to N was named pAOGDH-M76-G59N; a plasmid containing a modified FADGDHRR having a substitution at position 59 to P was named pAOGDH-M76-G59P; a plasmid containing a modified FADGDHRR having a substitution at position 59 to Q was named pAOGDH-M76-G59Q; a plasmid containing a modified FADGDHRR having a substitution at position 59 to R was named pAOGDH-M76-G59R; a plasmid containing a modified FADGDHRR having a substitution at position 59 to S was named pAOGDH-M76-G59S; a plasmid containing a modified FADGDHRR having a substitution at position 59 to T was named pAOGDH-M76-G59T; a plasmid containing a modified FADGDHRR having a substitution at position 59 to V was named pAOGDH-M76-G59V; a plasmid containing a modified FADGDHRR having a substitution at position 59 to W was named pAOGDH-M76-G59W; and a plasmid containing a modified FADGDH having a substitution at position 59 to Y was named pAOGDH-M76-G59Y.

Example C5

Comparison of Temperature Dependencies and Actions to Xylose of Modified FADGDHs Having Optimized Amino Acids at Position 59

Measurements of temperature dependencies and actions to xylose were performed for the modified FADGDHs in which the amino acid at position 59 was substituted with 19 types of amino acids using a method similar to that in Example C3. The results of the temperature dependencies and actions to xylose of the modified FADGDHs are shown in Table 4.

Table 4 shows the results of comparison of temperature dependencies and actions to xylose of the modified FADGDHs having a modification at position G59 when culturing was performed for 24 hours at 30° C. in 5 ml LB medium/test tubes.

Temperature dependencies were improved when compared to the pre-modified FADGDH, in the modified FADGDH having a substitution at position 59 to A, the modified FADGDH having a substitution at position 59 to C, the modified FADGDH having a substitution at position 59 to D, the modified FADGDH having a substitution at position 59 to F, the modified FADGDH having a substitution at position 59 to H, the modified FADGDH having a substitution at position 59 to K, the modified FADGDH having a substitution at position 59 to L, the modified FADGDH having a substitution at position 59 to M, the modified FADGDH having a substitution at position 59 to N, the modified FADGDH having a substitution at position 59 to P, the modified FADGDH having a substitution at position 59 to Q, the modified FADGDH having a substitution at position 59 to S, the modified FADGDH having a substitution at position 59 to T, the modified FADGDH having a substitution at position 59 to W, and in the modified FADGDH having a substitution at position 59 to Y. Furthermore, not only the temperature dependencies were improved, but also actions to xylose were reduced when compared to the pre-modified FADGDH, in the modified FADGDH having a substitution at position 59 to C, the modified FADGDH having a substitution at position 59 to D, the modified FADGDH having a substitution at position 59 to K, the modified FADGDH having a substitution at position 59 to M, the modified FADGDH having a substitution at position 59 to Q, the modified FADGDH having a substitution at position 59 to S, and the modified FADGDH having a substitution at position 59 to T.

TABLE 4

Comparison of temperature dependencies and actions to xylose of modified FADGDHs in which G59 is substituted with 19 types of amino acids

| Variant | Temperature dependency (%) | Temperature dependency ratio (taking Mut1 as 1) | Action to xylose (%) | Ratio of action to xylose (taking Mut1 as 1) |
|---|---|---|---|---|
| Mut1 | 62.55 | 1.00 | 10.30 | 1.00 |
| A | 66.46 | 1.06 | 10.39 | 1.01 |
| C | 72.88 | 1.17 | 9.91 | 0.96 |
| D | 64.23 | 1.03 | 9.97 | 0.97 |
| E | inactivated | — | inactivated | — |
| F | 75.86 | 1.21 | 15.80 | 1.53 |
| H | 71.32 | 1.14 | 11.58 | 1.12 |
| I | inactivated | — | inactivated | — |
| K | 70.41 | 1.13 | 9.79 | 0.95 |
| L | 71.93 | 1.15 | 23.98 | 2.33 |
| M | 75.47 | 1.21 | 8.26 | 0.80 |
| N | 70.13 | 1.12 | 10.71 | 1.04 |
| P | 68.24 | 1.09 | 13.12 | 1.27 |
| Q | 70.67 | 1.13 | 8.80 | 0.85 |
| R | inactivated | — | inactivated | — |
| S | 65.66 | 1.05 | 9.87 | 0.96 |
| T | 75.05 | 1.20 | 9.60 | 0.93 |
| V | inactivated | — | inactivated | — |
| W | 70.84 | 1.13 | 13.79 | 1.34 |
| Y | 76.86 | 1.23 | 17.47 | 1.70 |

Example D1

Creating Modified FADGDH Gene

A commercially available *Escherichia coli* competent cell (*E. coli* DH5a; product of Toyobo Co., Ltd.) was transformed using a recombinant plasmid pAOGDH-M76 that contains the gene (SEQ ID NO: 5) encoding the FADGDH of SEQ ID NO: 2. Transformed cells were applied on an agar medium (1% polypeptone, 0.5% yeast extract, 0.5% NaCl, 1.5% agar; pH 7.3) containing ampicillin, and cultured overnight at 30° C. The obtained transformant was inoculated to a liquid medium (1% polypeptone, 0.5% yeast extract, 0.5% NaCl; pH 7.3) containing ampicillin (50 mg/ml; Nacalai Tesque, Inc.), and cultured overnight at 30° C. by shaking. A plasmid was prepared from the obtained microbial cells using a method commonly used in the art.

Using the plasmid as a template, a modified FADGDH was created using a synthetic oligonucleotide of SEQ ID NO: 22 designed such that asparagine at position 504 is substituted with serine and a synthetic oligonucleotide complementary thereto, in QuikChange™ Site-Directed Mutagenesis Kit (product of Stratagene Corp.).

Example D2

Preparation of Plasmid with Modified FADGDH

A commercially available *Escherichia coli* competent cell (*E. coli* DH5a; product of Toyobo Co., Ltd.) was transformed using the obtained modified FADGDH, and cultured for 16 hours at 37° C. in an LB agar medium containing ampicillin. Then, a single colony of the modified FADGDH was inoculated to an LB liquid medium containing ampicillin, and cultured overnight at 30° C. by shaking. A plasmid was extracted from the obtained microbial cells using a method commonly used in the art. Relevant positions in the extracted plasmid were identified using a DNA sequencer (ABI Prism™ 3700 DNA Analyzer; product of Perkin-Elmer Inc.), and the modified FADGDH having a substitution with the amino acid described in Example D1 was obtained. The plasmid in which asparagine at position 504 was substituted with serine was named pAOGDH-M76-N504S.

Example D3

Preparation of Crude Enzyme Liquid Containing Modified FADGDH, and Comparison of Temperature Dependencies and Actions to Xylose A commercially available *Escherichia coli* competent cell (*E. coli* DH5a; product of Toyobo Co., Ltd.) was transformed using pAOGDH-M76-N504S obtained in Example D2, and cultured for 16 hours at 37° C. in an LB agar medium containing ampicillin. Then, a single colony of the modified FADGDH was inoculated to an LB liquid medium containing ampicillin, and cultured overnight at 30° C. by shaking. Microbial cells obtained from one portion of the culture medium using centrifugal separation were collected, and the microbial cells were homogenized in 50 mM phosphate buffer (pH 6.0) using glass beads to prepare a crude enzyme liquid.

By using the prepared crude enzyme liquid, GDH activity at 25° C. and 37° C., and action to xylose at 37° C. were measured using the above described activity measuring method. The results are shown in Table 5.

Table 5 shows the results of comparison of temperature dependency of N504S when culturing was performed for 24 hours at 30° C. in a 5 ml LB medium/test tube.

Comparing the modified sites and temperature dependencies, an advantageous effect was confirmed that substituting asparagine at position 504 with serine had improved temperature dependency when compared to the pre-modified FADGDH (hereinafter, also represented as Mut1), and thereby, optimization of amino acid was performed at position 504 and a detailed investigation was conducted.

TABLE 5

Comparison of temperature dependency of modified FADGDH

| Variant | Temperature dependency (%) | Temperature dependency ratio (taking Mut1 as 1) |
|---|---|---|
| Mut1 | 62.55 | 1.00 |
| N504S | 71.50 | 1.14 |

Example D4

Optimization of Amino Acid at Position 504

Using pAOGDH-M76 used in Example C1 as a template, modified FADGDHs were created using synthetic oligonucleotides of SEQ ID NO: 26 designed such that asparagine at position 504 is substituted with the 7 other types of amino acids and synthetic oligonucleotides complementary thereto, in QuikChange™ Site-Directed Mutagenesis Kit (product of Stratagene Corp.). A commercially available *Escherichia coli* competent cell (*E. coli* DH5a; product of Toyobo Co., Ltd.) was transformed using the modified FADGDH, and cultured for 16 hours at 37° C. in an LB agar medium containing ampicillin. Then, a single colony having the modified FADGDH was inoculated to an LB liquid medium containing ampicillin, and cultured overnight at 30° C. by shaking. Next, 1 ml of the culture medium was taken and a plasmid was extracted using a method commonly used in the art. Relevant positions in the extracted plasmid were identified using a DNA sequencer (ABI Prism™ 3700 DNA Analyzer; product of Perkin-Elmer Inc.). A plasmid containing a modified FADGDH having a substitution at position 504 to A was named pAOGDH-M76-N504A; a plasmid containing a modified FADGDH having a substitution at position 504 to D was named pAOGDH-M76-N504D; a plasmid containing a modified FADGDH having a substitution at position 504 to G was named pAOGDH-M76-N504G; a plasmid containing a modified FADGDH having a substitution at position 504 to L was named pAOGDH-M76-N504L; a plasmid containing a modified FADGDH having a substitution at position 504 to R was named pAOGDH-M76-N504R; a plasmid containing a modified FADGDH having a substitution at position 504 to S was named pAOGDH-M76-N504S; and a plasmid containing a modified FADGDH having a substitution at position 504 to T was named pAOGDH-M76-N504T.

Example D5

Comparison of Temperature Dependencies and Actions to Xylose of Modified FADGDHs Having Optimized Amino Acids at Position 504

Measurements of temperature dependencies and actions to xylose were performed for the modified FADGDHs in which the amino acid at position 504 was substituted with 7 types of amino acids using a method similar to that in Example D3. The results of the temperature dependencies and actions to xylose of the modified FADGDHs are shown in Table 6.

Table 6 shows the results of comparison of temperature dependencies and actions to xylose of the modified FADGDHs having modifications at position N504 when culturing was performed for 24 hours at 30° C. in 5 ml LB medium/test tubes.

Temperature dependencies were improved when compared to the pre-modified FADGDH (Mut1), in the modified FADGDH having a substitution at position 504 to G and the modified FADGDH having a substitution at position 504 to S. Furthermore, not only the temperature dependencies were improved, but also actions to xylose were reduced when compared to the pre-modified FADGDH (Mut1) in the modified FADGDH having a substitution at position 504 to G.

TABLE 6

Comparison of temperature dependencies and actions to xylose of modified FADGDHs having a substitution at N504 with 7 types of amino acids

| Variant | Temperature dependency (%) | Temperature dependency ratio (taking Mut1 as 1) | Action to xylose (%) | Ratio of action to xylose (taking Mut1 as 1) |
|---|---|---|---|---|
| Mut1 | 62.55 | 1.00 | 10.30 | 1.00 |
| A | inactivated | — | inactivated | — |
| D | inactivated | — | inactivated | — |
| G | 78.30 | 1.25 | 9.52 | 0.92 |
| L | inactivated | — | inactivated | — |
| R | inactivated | — | inactivated | — |
| S | 71.50 | 1.14 | 11.61 | 1.13 |
| T | inactivated | — | inactivated | — |

Example E1

Creating Modified FADGDH Gene

A commercially available *Escherichia coli* competent cell (*E. coli* DH5a; product of Toyobo Co., Ltd.) was transformed using a recombinant plasmid pAOGDH-M76 that contains the gene (SEQ ID NO: 5) encoding the FADGDH of SEQ ID NO: 2. Transformed cells were applied on an LB agar medium (1.0% polypeptone, 0.5% yeast extract, 1.0% NaCl, 1.5% agar; pH 7.3) containing ampicillin, and cultured overnight at 30° C. The obtained transformant was inoculated to an LB liquid medium (1% polypeptone, 0.5% yeast extract, 1.0% NaCl; pH 6.5) containing ampicillin (50 mg/ml; product of Nacalai Tesque, Inc.), and cultured overnight at 30° C. by shaking. A plasmid was prepared from the obtained microbial cells using a method commonly used in the art.

Example E2

Optimization of Amino Acid G53

Using pAOGDH-M76 used in Example E1 as a template, PCR was performed using synthetic oligonucleotides of SEQ ID NO: 27 designed such that glycine at position 53 is substituted with other amino acids and synthetic oligonucleotides complementary thereto, in QuikChange™ Site-Directed Mutagenesis Kit (product of Stratagene Corp.). Then, a commercially available *Escherichia coli* competent cell (*E. coli* DH5a; product of Toyobo Co., Ltd.) was transformed using the PCR product, and cultured for 16 hours at 37° C. in an LB agar medium containing ampicillin. Next, a single colony having the modified FADGDH was inoculated to an LB liquid medium containing ampicillin, and cultured overnight at 30° C. by shaking. Then, 1 ml of the culture medium was taken, and a plasmid was extracted using a method commonly used in the art. Relevant positions in the extracted plasmid were identified using a DNA sequencer (ABI Prism™ 3700 DNA Analyzer; product of Perkin-Elmer Inc.). A plasmid containing a modified FADGDH having a substitution at position 53 to F was named pAOGDH-M76-G53F; a plasmid containing a modified FADGDH having a substitution at position 53 to I was named pAOGDH-M76-G53I; a plasmid containing a modified FADGDH having a substitution at position 53 to L was named pAOGDH-M76-G53L; a plasmid containing a modified FADGDH having a substitution at position 53 to P was named pAOGDH-M76-G53P; a plasmid containing a modified FADGDH having a substitution at position 53 to Q was named pAOGDH-M76-G53Q; a plasmid containing a modified FADGDH having a substitution at position 53 to R was named pAOGDH-M76-G53R; a plasmid containing a modified FADGDH having a substitution at position 53 to S was named pAOGDH-M76-G53S; a plasmid containing a modified FADGDH having a substitution at position 53 to W was named pAOGDH-M76-G53W; and a plasmid containing a modified FADGDH having a substitution at position 53 to Y was named pAOGDH-M76-G53Y.

Example E3

Evaluation of Temperature Dependencies and Actions to Xylose of Modified FADGDHs Having Optimized Amino Acids at Position 53

Batches of *Escherichia coli* DH5a were transformed with the respective modified FADGDH plasmids having a substitution at position 53 acquired in Example E2 with other amino acids, and cultured for 16 hours at 37° C. in LB agar media containing ampicillin. Then, a single colony of each of the modified FADGDHs was inoculated to an LB liquid medium containing ampicillin, and cultured overnight at 30° C. by shaking. Microbial cells obtained from one portion of each of the culture media using centrifugal separation were collected, and the microbial cells were homogenized in 50 mM phosphate buffer (pH 6.0) using glass beads to prepare crude enzyme liquids. By using the prepared crude enzyme liquids, GDH activities at 25° C. and 37° C., and actions to xylose at 37° C. were measured using the above described activity measuring method. The results are shown in Table 7.

Table 7 shows the results of comparison of temperature dependencies and actions to xylose of the modified FADGDHs having modifications at position 53 when culturing was performed for 24 hours at 30° C. in 5 ml LB medium/test tubes.

The modified FADGDHs having a substitution at position 53 to F, L, Q, R, S, W, and Y not only had improved temperature dependencies, but also had reduced actions to xylose when compared to the pre-modified FADGDH (Mut1).

TABLE 7

Comparison of temperature dependencies and actions to xylose of modified FADGDHs having a substitution at G53 to other amino acids

| Variant | Temperature dependency (%) | Temperature dependency ratio (taking Mut1 as 1) | Action to xylose (%) | Ratio of action to xylose (taking Mut1 as 1) |
|---|---|---|---|---|
| Mut1 | 62.55 | 1.00 | 10.50 | 1.00 |
| F | 69.07 | 1.10 | 5.87 | 0.56 |
| I | N.D. | N.D. | N.D. | N.D. |
| L | 68.51 | 1.10 | 3.74 | 0.36 |
| P | N.D. | N.D. | N.D. | N.D. |

TABLE 7-continued

Comparison of temperature dependencies and actions to xylose of modified FADGDHs having a substitution at G53 to other amino acids

| Variant | Temperature dependency (%) | Temperature dependency ratio (taking Mut1 as 1) | Action to xylose (%) | Ratio of action to xylose (taking Mut1 as 1) |
|---|---|---|---|---|
| Q | 67.30 | 1.08 | 6.15 | 0.59 |
| R | 73.04 | 1.17 | 3.12 | 0.30 |
| S | 69.61 | 1.11 | 4.70 | 0.45 |
| W | 68.88 | 1.10 | 9.37 | 0.89 |
| Y | 68.77 | 1.10 | 7.72 | 0.74 |

Example E4

Optimization of Amino Acid at Position 60

With a method similar to that in Example E2, optimization of amino acid was conducted using synthetic oligonucleotides of SEQ ID NO: 29 designed such that the amino acid at position 60 is substituted with 20 types of amino acids, and synthetic oligonucleotides complementary thereto. A plasmid containing a modified FADGDH having a substitution at position 60 to C was named pAOGDH-M76-S60C; a plasmid containing a modified FADGDH having a substitution at position 60 to D was named pAOGDH-M76-S60D; a plasmid containing a modified FADGDH having a substitution at position 60 to G was named pAOGDH-M76-S60G; a plasmid containing a modified FADGDH having a substitution at position 60 to I was named pAOGDH-M76-S60I; a plasmid containing a modified FADGDH having a substitution at position 60 to K was named pAOGDH-M76-S60K; a plasmid containing a modified FADGDH having a substitution at position 60 to L was named pAOGDH-M76-S60L; a plasmid containing a modified FADGDH having a substitution at position 60 to N was named pAOGDH-M76-S60N; a plasmid containing a modified FADGDH having a substitution at position 60 to T was named pAOGDH-M76-S60T; a plasmid containing a modified FADGDH having a substitution at position 60 to V was named pAOGDH-M76-S60V; and a plasmid containing a modified FADGDH having a substitution at position 60 to Y was named pAOGDH-M76-S60Y.

Example E5

Comparison of Temperature Dependencies and Actions to Xylose of Modified FADGDHs Having Optimized Amino Acids at Position 60

With a method similar to that in Example E3, crude enzyme liquids of the modified FADGDHs were prepared, and temperature dependencies and actions to xylose were measured. The results of the temperature dependencies and actions to xylose of the modified FADGDHs are shown in Table 8.

Table 8 shows the results of comparison of temperature dependencies and actions to xylose of the modified FADGDHs having modifications at position S60 when culturing was performed for 24 hours at 30° C. in 5 ml LB medium/test tubes.

The modified FADGDHs, having a substitution at position 60 to C, D, G, and N, not only had reduced temperature dependencies but also had reduced actions to xylose when compared to the pre-modified FADGDH (Mut1). Furthermore, the modified FADGDHs having a substitution at position 60 to L, T, and V had improved temperature dependencies when compared to the pre-modified FADGDH (Mut1).

TABLE 8

Comparison of temperature dependencies and actions to xylose of modified FADGDHs having a substitution at S60 to 9 types of amino acids

| Variant | Temperature dependency (%) | Temperature dependency ratio (taking Mut1 as 1) | Action to xylose (%) | Ratio of action to xylose (taking Mut1 as 1) |
|---|---|---|---|---|
| Mut1 | 62.55 | 1.00 | 10.30 | 1.00 |
| C | 82.36 | 1.32 | 5.16 | 0.50 |
| D | 68.93 | 1.10 | 9.30 | 0.90 |
| G | 64.74 | 1.03 | 9.10 | 0.88 |
| I | N.D. | N.D. | N.D. | N.D. |
| K | 62.74 | 1.00 | 10.23 | 0.99 |
| L | 68.86 | 1.10 | 12.74 | 1.24 |
| N | 68.04 | 1.09 | 7.79 | 0.76 |
| T | 63.00 | 1.01 | 10.14 | 0.98 |
| V | 67.56 | 1.08 | 15.06 | 1.46 |
| Y | 62.05 | 0.99 | 10.11 | 0.98 |

INDUSTRIAL APPLICABILITY

Usage of an FAD dependent glucose dehydrogenase of the present invention having improved temperature dependency allows improving precision of glucose measurement, and has a large contribution to industries in medical related fields and the like.

---

The invention claimed is:

1. A protein of the following (1) or (2):
   (1) a protein comprising the amino acid sequence set forth in SEQ ID NO:2 having one or more amino acid substitutions selected from the group consisting of S60C, S60D, S60L, S60N, S60V, S60G, S60T, N504G, and N504S, and having a glucose dehydrogenase activity,
   (2) a protein comprising an amino acid sequence having at least 90% sequence identity to the amino acid sequence set forth in SEQ ID NO: 2 having one or more amino acids selected from the group consisting of 60C, 60D, 60L, 60N, 60V, 60G, 60T, 504G, and 504S, and having a glucose dehydrogenase activity.

2. A polynucleotide that encodes an amino acid sequence of the protein according to claim 1.

3. A vector that contains the polynucleotide according to claim 2.

4. A transformant transformed with the vector according to claim 3.

5. A method for producing a protein having a glucose dehydrogenase activity, the method comprising culturing the transformant according to claim 4.

6. A glucose assay kit comprising the protein according to claim 1.

7. A glucose sensor comprising the protein according to claim 1.

8. A method for measuring glucose level in a sample, comprising contacting a sample that contains glucose with a protein according to claim 1 and measuring a value that correlates to the amount of glucose in the sample.

9. A protein comprising the amino acid sequence set forth in SEQ ID NO:2 having a S60C amino acid substitution and having a glucose dehydrogenase activity.

10. A protein comprising the amino acid sequence set forth in SEQ ID NO:2 having a N504G amino acid substitution and having a glucose dehydrogenase activity.

* * * * *

SEQUENCE LISTING

```
<160> NUMBER OF SEQ ID NOS: 54

<210> SEQ ID NO 1
<211> LENGTH: 572
<212> TYPE: PRT
<213> ORGANISM: Aspergillus oryzae

<400> SEQUENCE: 1

Met Lys Asn Thr Thr Thr Tyr Asp Tyr Ile Val Val Gly Gly Gly Thr
1               5                   10                  15

Ser Gly Leu Val Val Ala Asn Arg Leu Ser Glu Asn Pro Asp Val Ser
            20                  25                  30
```

Val Leu Leu Leu Glu Ala Gly Ala Ser Val Phe Asn Asn Pro Asp Val
                35                  40                  45

Thr Asn Ala Asn Gly Tyr Gly Leu Ala Phe Gly Ser Ala Ile Asp Trp
 50                  55                  60

Gln Tyr Gln Ser Ile Asn Gln Ser Tyr Ala Gly Gly Lys Gln Gln Val
 65                  70                  75                  80

Leu Arg Ala Gly Lys Ala Leu Gly Gly Thr Ser Thr Ile Asn Gly Met
                 85                  90                  95

Ala Tyr Thr Arg Ala Glu Asp Val Gln Ile Asp Val Trp Gln Lys Leu
                100                 105                 110

Gly Asn Glu Gly Trp Thr Trp Lys Asp Leu Leu Pro Tyr Tyr Leu Lys
                115                 120                 125

Ser Glu Asn Leu Thr Ala Pro Thr Ser Ser Gln Val Ala Ala Gly Ala
    130                 135                 140

Ala Tyr Asn Pro Ala Val Asn Gly Lys Glu Gly Pro Leu Lys Val Gly
145                 150                 155                 160

Trp Ser Gly Ser Leu Ala Ser Gly Asn Leu Ser Val Ala Leu Asn Arg
                165                 170                 175

Thr Phe Gln Ala Ala Gly Val Pro Trp Val Glu Asp Val Asn Gly Gly
                180                 185                 190

Lys Met Arg Gly Phe Asn Ile Tyr Pro Ser Thr Leu Asp Val Asp Leu
                195                 200                 205

Asn Val Arg Glu Asp Ala Ala Arg Ala Tyr Tyr Phe Pro Tyr Asp Asp
    210                 215                 220

Arg Lys Asn Leu His Leu Leu Glu Asn Thr Thr Ala Asn Arg Leu Phe
225                 230                 235                 240

Trp Lys Asn Gly Ser Ala Glu Glu Ala Ile Ala Asp Gly Val Glu Ile
                245                 250                 255

Thr Ser Ala Asp Gly Lys Val Thr Arg Val His Ala Lys Lys Glu Val
                260                 265                 270

Ile Ile Ser Ala Gly Ala Leu Arg Ser Pro Leu Ile Leu Glu Leu Ser
            275                 280                 285

Gly Val Gly Asn Pro Thr Ile Leu Lys Lys Asn Asn Ile Thr Pro Arg
    290                 295                 300

Val Asp Leu Pro Thr Val Gly Glu Asn Leu Gln Asp Gln Phe Asn Asn
305                 310                 315                 320

Gly Met Ala Gly Glu Gly Tyr Gly Val Leu Ala Gly Ala Ser Thr Val
                325                 330                 335

Thr Tyr Pro Ser Ile Ser Asp Val Phe Gly Asn Glu Thr Asp Ser Ile
                340                 345                 350

Val Ala Ser Leu Arg Ser Gln Leu Ser Asp Tyr Ala Ala Ala Thr Val
            355                 360                 365

Lys Val Ser Asn Gly His Met Lys Gln Glu Asp Leu Glu Arg Leu Tyr
    370                 375                 380

Gln Leu Gln Phe Asp Leu Ile Val Lys Asp Lys Val Pro Ile Ala Glu
385                 390                 395                 400

Ile Leu Phe His Pro Gly Gly Asn Ala Val Ser Ser Glu Phe Trp
                405                 410                 415

Gly Leu Leu Pro Phe Ala Arg Gly Asn Ile His Ile Ser Ser Asn Asp
            420                 425                 430

Pro Thr Ala Pro Ala Ala Ile Asn Pro Asn Tyr Phe Met Phe Glu Trp
    435                 440                 445

Asp Gly Lys Ser Gln Ala Gly Ile Ala Lys Tyr Ile Arg Lys Ile Leu
                450                 455                 460

```
Arg Ser Ala Pro Leu Asn Lys Leu Ile Ala Lys Glu Thr Lys Pro Gly
465                 470                 475                 480

Leu Ser Glu Ile Pro Ala Thr Ala Ala Asp Glu Lys Trp Val Glu Trp
            485                 490                 495

Leu Lys Ala Asn Tyr Arg Ser Asn Phe His Pro Val Gly Thr Ala Ala
                500                 505                 510

Met Met Pro Arg Ser Ile Gly Gly Val Val Asp Asn Arg Leu Arg Val
            515                 520                 525

Tyr Gly Thr Ser Asn Val Arg Val Asp Ala Ser Val Leu Pro Phe
            530                 535                 540

Gln Val Cys Gly His Leu Val Ser Thr Leu Tyr Ala Val Ala Glu Arg
545                 550                 555                 560

Ala Ser Asp Leu Ile Lys Glu Asp Ala Lys Ser Ala
                565                 570

<210> SEQ ID NO 2
<211> LENGTH: 572
<212> TYPE: PRT
<213> ORGANISM: Aspergillus oryzae

<400> SEQUENCE: 2

Met Lys Asn Thr Thr Thr Tyr Asp Tyr Ile Val Val Gly Gly Gly Thr
1               5                   10                  15

Ser Gly Leu Val Val Ala Asn Arg Leu Ser Glu Asn Pro Asp Val Ser
                20                  25                  30

Val Leu Leu Leu Glu Ala Gly Ala Ser Val Phe Asn Asn Pro Asp Val
            35                  40                  45

Thr Asn Ala Asn Gly Tyr Gly Leu Ala Phe Gly Ser Ala Ile Asp Trp
50                  55                  60

Gln Tyr Gln Ser Ile Asn Gln Ser Tyr Ala Gly Gly Lys Gln Gln Val
65                  70                  75                  80

Leu Arg Ala Gly Lys Ala Leu Gly Gly Thr Ser Thr Ile Asn Gly Met
                85                  90                  95

Ala Tyr Thr Arg Ala Glu Asp Val Gln Ile Asp Val Trp Gln Lys Leu
            100                 105                 110

Gly Asn Glu Gly Trp Thr Trp Lys Asp Leu Leu Pro Tyr Tyr Leu Lys
        115                 120                 125

Ser Glu Asn Leu Thr Ala Pro Thr Ser Ser Gln Val Ala Ala Gly Ala
130                 135                 140

Ala Tyr Asn Pro Ala Val Asn Gly Lys Glu Gly Pro Leu Lys Val Gly
145                 150                 155                 160

Trp Ser Arg Ser Leu Ala Ser Gly Asn Leu Ser Val Ala Leu Asn Arg
                165                 170                 175

Thr Phe Gln Ala Ala Gly Val Pro Trp Val Glu Asp Val Asn Gly Gly
            180                 185                 190

Lys Met Arg Gly Phe Asn Ile Tyr Pro Ser Thr Leu Asp Val Asp Leu
        195                 200                 205

Asn Val Arg Glu Asp Ala Ala Arg Ala Tyr Tyr Phe Pro Tyr Asp Asp
210                 215                 220

Arg Lys Asn Leu His Leu Leu Glu Asn Thr Thr Ala Asn Arg Leu Phe
225                 230                 235                 240

Trp Lys Asn Gly Ser Ala Glu Glu Ala Ile Ala Asp Gly Val Glu Ile
                245                 250                 255

Thr Ser Ala Asp Gly Lys Val Thr Arg Val His Ala Lys Lys Glu Val
            260                 265                 270
```

Ile Ile Ser Ala Gly Ala Leu Arg Ser Pro Leu Ile Leu Glu Leu Ser
            275                 280                 285

Gly Val Gly Asn Pro Thr Ile Leu Lys Lys Asn Asn Ile Thr Pro Arg
        290                 295                 300

Val Asp Leu Pro Thr Val Gly Glu Asn Leu Gln Asp Gln Phe Asn Asn
305                 310                 315                 320

Gly Met Ala Gly Glu Gly Tyr Gly Val Leu Ala Gly Ala Ser Thr Val
                325                 330                 335

Thr Tyr Pro Ser Ile Ser Asp Val Phe Gly Asn Glu Thr Asp Ser Ile
            340                 345                 350

Val Ala Ser Leu Arg Ser Gln Leu Ser Asp Tyr Ala Ala Ala Thr Val
        355                 360                 365

Lys Val Ser Asn Gly His Met Lys Gln Glu Asp Leu Glu Arg Leu Tyr
    370                 375                 380

Gln Leu Gln Phe Asp Leu Ile Val Lys Asp Lys Val Pro Ile Ala Glu
385                 390                 395                 400

Ile Leu Phe His Pro Gly Gly Asn Ala Val Ser Ser Glu Phe Trp
                405                 410                 415

Gly Leu Leu Pro Phe Ala Arg Gly Asn Ile His Ile Ser Ser Asn Asp
            420                 425                 430

Pro Thr Ala Pro Ala Ala Ile Asn Pro Asn Tyr Phe Met Phe Glu Trp
        435                 440                 445

Asp Gly Lys Ser Gln Ala Gly Ile Ala Lys Tyr Ile Arg Lys Ile Leu
    450                 455                 460

Arg Ser Ala Pro Leu Asn Lys Leu Ile Ala Lys Glu Thr Lys Pro Gly
465                 470                 475                 480

Leu Ser Glu Ile Pro Ala Thr Ala Ala Asp Glu Lys Trp Val Glu Trp
                485                 490                 495

Leu Lys Ala Asn Tyr Arg Ser Asn Phe His Pro Val Gly Thr Ala Ala
            500                 505                 510

Met Met Pro Arg Ser Ile Gly Gly Val Val Asp Asn Arg Leu Arg Val
        515                 520                 525

Tyr Gly Thr Ser Asn Val Arg Val Asp Ala Ser Val Leu Pro Phe
    530                 535                 540

Gln Val Cys Gly His Leu Cys Ser Thr Leu Tyr Ala Val Ala Glu Arg
545                 550                 555                 560

Ala Ser Asp Leu Ile Lys Glu Asp Ala Lys Ser Ala
                565                 570

<210> SEQ ID NO 3
<211> LENGTH: 568
<212> TYPE: PRT
<213> ORGANISM: Aspergillus terreus

<400> SEQUENCE: 3

Met Lys Tyr Asp Tyr Ile Val Ile Gly Gly Thr Ser Gly Leu Ala
1               5                   10                  15

Val Ala Asn Arg Leu Ser Glu Asp Pro Ser Val Asn Val Leu Ile Leu
            20                  25                  30

Glu Ala Gly Gly Ser Val Trp Asn Asn Pro Asn Val Thr Asn Val Asn
        35                  40                  45

Gly Tyr Gly Leu Ala Phe Gly Ser Asp Ile Asp Trp Gln Tyr Gln Ser
    50                  55                  60

Val Asn Gln Pro Tyr Gly Gly Asn Val Ser Gln Val Leu Arg Ala Gly
65                  70                  75                  80

-continued

Lys Ala Leu Gly Gly Thr Ser Thr Ile Asn Gly Met Ala Tyr Thr Arg
                    85                  90                  95

Ala Glu Asp Val Gln Ile Asp Ala Trp Glu Thr Ile Gly Asn Thr Gly
            100                 105                 110

Trp Thr Trp Lys Asn Leu Phe Pro Tyr Tyr Arg Lys Ser Glu Asn Phe
            115                 120                 125

Thr Val Pro Thr Lys Ser Gln Thr Ser Leu Gly Ala Ser Tyr Glu Ala
            130                 135                 140

Gly Ala His Gly His Glu Gly Pro Leu Asp Val Ala Phe Thr Gln Ile
145                 150                 155                 160

Glu Ser Asn Asn Leu Thr Thr Tyr Leu Asn Arg Thr Phe Gln Gly Met
                165                 170                 175

Gly Leu Pro Trp Thr Glu Asp Val Asn Gly Gly Lys Met Arg Gly Phe
            180                 185                 190

Asn Leu Tyr Pro Ser Thr Val Asn Leu Glu Glu Tyr Val Arg Glu Asp
            195                 200                 205

Ala Ala Arg Ala Tyr Tyr Trp Pro Tyr Lys Ser Arg Pro Asn Leu His
210                 215                 220

Val Leu Leu Asn Thr Phe Ala Asn Arg Ile Val Trp Asp Gly Glu Ala
225                 230                 235                 240

Arg Asp Gly Asp Ile Thr Ala Ser Gly Val Glu Ile Thr Ser Arg Asn
                245                 250                 255

Gly Thr Val Arg Val Ile Asn Ala Glu Lys Glu Val Ile Val Ser Ala
            260                 265                 270

Gly Ala Leu Lys Ser Pro Ala Ile Leu Glu Leu Ser Gly Ile Gly Asn
            275                 280                 285

Pro Ser Val Leu Asp Lys Tyr Asn Ile Pro Val Lys Val Asn Leu Pro
            290                 295                 300

Thr Val Gly Glu Asn Leu Gln Asp Gln Val Asn Ser His Met Asp Ala
305                 310                 315                 320

Ser Gly Asn Thr Ser Ile Ser Gly Thr Lys Ala Val Ser Tyr Pro Asp
                325                 330                 335

Val Tyr Asp Val Phe Gly Asp Glu Ala Glu Ser Val Ala Lys Gln Ile
            340                 345                 350

Arg Ala Ser Leu Lys Gln Tyr Ala Ala Asp Thr Ala Gln Ala Asn Gly
            355                 360                 365

Asn Ile Met Lys Ala Ala Asp Leu Glu Arg Leu Phe Glu Val Gln Tyr
            370                 375                 380

Asp Leu Ile Phe Lys Gly Arg Val Pro Ile Ala Glu Val Leu Asn Tyr
385                 390                 395                 400

Pro Gly Ser Ala Thr Ser Val Phe Ala Glu Phe Trp Ala Leu Leu Pro
                405                 410                 415

Phe Ala Arg Gly Ser Val His Ile Gly Ser Ser Asn Pro Val Glu Phe
            420                 425                 430

Pro Val Ile Asn Pro Asn Tyr Phe Met Leu Asp Trp Asp Ala Lys Ser
            435                 440                 445

Tyr Val Ala Val Ala Lys Tyr Ile Arg Arg Ser Phe Glu Ser Tyr Pro
            450                 455                 460

Leu Ser Ser Ile Val Lys Glu Ser Thr Pro Gly Tyr Asp Val Ile Pro
465                 470                 475                 480

Arg Asn Ala Ser Glu Gln Ser Trp Lys Glu Trp Val Phe Asp Lys Asn
                485                 490                 495

Tyr Arg Ser Asn Phe His Pro Val Gly Thr Ala Ala Met Met Pro Arg

```
                   500                505                510
Glu Ile Gly Gly Val Val Asp Glu Arg Leu Asn Val Tyr Gly Thr Thr
            515                 520                 525

Asn Val Arg Val Val Asp Ala Ser Val Leu Pro Phe Gln Val Cys Gly
        530                 535                 540

His Leu Val Ser Thr Leu Tyr Ala Val Ala Glu Arg Ala Ala Asp Leu
545                 550                 555                 560

Ile Lys Ala Asp Ala Gly Arg Arg
                565

<210> SEQ ID NO 4
<211> LENGTH: 1719
<212> TYPE: DNA
<213> ORGANISM: Aspergillus oryzae

<400> SEQUENCE: 4
atgaagaaca ctacgacata cgactacatc gttgtgggag gcggcacaag tggtcttgtg      60
gtcgcaaatc gcctttctga gaaccccgat gtctccgttc ttctgcttga ggccggtgct     120
tctgtgttca acaacccgga cgtaaccaac gctaacggtt atggattggc ctttggctcg     180
gccatcgact ggcagtacca gtctattaac aaaagctatg caggaggtaa acagcaagtt     240
ctgcgtgctg gtaaggccct tggaggaacc agtacaatca atggaatggc ctatacccgc     300
gcagaggatg tccagattga cgtttggcag aaacttggaa cgaaggttg gacgtggaaa     360 gatctcctac catactacct gaagagtgaa aacttgacgg cccctaccag ctctcaggtt     420
gctgctggcg ctgcttataa ccctgccgtg aatggaaaag aaggtcctct caaggtcggc     480
tggtcgggaa gcctggcctc cggtaatctg tcagttgctc tgaaccgtac gttccaagcc     540
gctggtgttc catgggttga ggatgtcaat ggaggcaaga tgcgtggctt caacatctac     600
ccatccaccc tcgacgttga cctcaatgtc cgcgaagatg cagcccgggc atactacttc     660
ccttatgatg acaggaagaa ccttcacctg ctggagaaca ccactgccaa ccgccttttc     720
tggaagaacg gctctgctga ggaagctatt gcggatggtg tcgagatcac ctccgctgat     780
ggcaaggtca ctcgtgtgca tgcaaagaaa gaggtcatca tctctgctgg tgccctgcgg     840
tctcctctca ttctcgagct ttcaggagtt ggaaacccaa ccatcctcaa aaagaacaac     900
ataaccccac gtgtcgatct ccccaccgtt ggggagaacc tccaagacca gttcaacaac     960
ggcatggctg gcgaaggata cggcgtcctt gccggtgcct caaccgtgac ctacccttcc    1020
atctccgacg tcttcggtaa cgagactgac tctatcgttg catctctccg atctcaactc    1080
tccgactacg ccgccgcgac cgtcaaggtc agcaacggcc acatgaagca ggaggacctt    1140
gagcgcctct accagctcca atttgacctc atcgtcaagg acaaggtccc tatcgccgag    1200
atcctcttcc accccggtgg tggaaacgcc gtgtcctccg aattctgggg cttgcttccc    1260
ttcgcccgtg gcaacatcca cattagctcc aatgacccga ctgctcccgc cgccatcaac    1320
cctaactact ttatgttcga atgggacggc aagagccagg ccggtatcgc caagtacatc    1380
aggaagattc tccgcagcgc accattgaac aaacttattg cgaaggaaac caagcccggt    1440
ctctctgaga ttccggccac tgctgcggat gagaagtggg ttgaatggct caaggctaac    1500
tatcgttcca acttccaccc cgtcggaact gctgccatga tgcctcgttc cattggtggc    1560
gttgttgata accgtctccg ggtctatggt accagcaatg ttcgcgtcgt agatgcgtct    1620
gtcctgccct tccaggtttg cggccacttg gttagcacgc tttatgccgt tgccgagcgc    1680
gcttccgact tgattaagga ggatgcgaag agtgcttag                           1719
```

<210> SEQ ID NO 5
<211> LENGTH: 1719
<212> TYPE: DNA
<213> ORGANISM: Aspergillus oryzae

<400> SEQUENCE: 5

| | | | | | |
|---|---|---|---|---|---|
| atgaagaaca | ctacgacata | cgactacatc | gttgtgggag | gcggcacaag | tggtcttgtg | 60 |
| gtcgcaaatc | gcctttctga | gaaccccgat | gtctccgttc | ttctgcttga | ggccggtgct | 120 |
| tctgtgttca | caacccgga | cgtaaccaac | gctaacggtt | atggattggc | ctttggctcg | 180 |
| gccatcgact | ggcagtacca | gtctattaac | caaagctatg | caggaggtaa | acagcaagtt | 240 |
| ctgcgtgctg | gtaaggccct | tggaggaacc | agtacaatca | tggaatggc | ctatacccgc | 300 |
| gcagaggatg | tccagattga | cgtttggcag | aaacttggaa | cgaaggttg | gacgtggaaa | 360 |
| gatctcctac | atactacct | gaagagtgaa | aacttgacgg | ccctaccag | ctctcaggtt | 420 |
| gctgctggcg | ctgcttataa | ccctgccgtg | aatggaaaag | aaggtcctct | caaggtcggc | 480 |
| tggtcgagga | gcctggcctc | cggtaatctg | tcagttgctc | tgaaccgtac | gttccaagcc | 540 |
| gctggtgttc | catgggttga | ggatgtcaat | ggaggcaaga | tgcgtggctt | caacatctac | 600 |
| ccatccaccc | tcgacgttga | cctcaatgtc | cgcgaagatg | cagcccgggc | atactacttc | 660 |
| ccttatgatg | acaggaagaa | ccttcacctg | ctggagaaca | ccactgccaa | ccgccttttc | 720 |
| tggaagaacg | gctctgctga | ggaagctatt | gcggatggtg | tcgagatcac | ctccgctgat | 780 |
| ggcaaggtca | ctcgtgtgca | tgcaaagaaa | gaggtcatca | tctctgctgg | tgccctgcgg | 840 |
| tctcctctca | ttctcgagct | ttcaggagtt | ggaaacccaa | ccatcctcaa | aaagaacaac | 900 |
| ataaccccac | gtgtcgatct | ccccaccgtt | ggggagaacc | tccaagacca | gttcaacaac | 960 |
| ggcatggctg | gcgaaggata | cggcgtcctt | gccggtgcct | caaccgtgac | ctacccttcc | 1020 |
| atctccgacg | tcttcggtaa | cgagactgac | tctatcgttg | catctctccg | atctcaactc | 1080 |
| tccgactacg | ccgccgcgac | cgtcaaggtc | agcaacggcc | acatgaagca | ggaggacctt | 1140 |
| gagcgcctct | accagctcca | atttgacctc | atcgtcaagg | acaaggtccc | tatcgccgag | 1200 |
| atcctcttcc | accccggtgg | tggaaacgcc | gtgtcctccg | aattctgggg | cttgcttccc | 1260 |
| ttcgcccgtg | caacatcca | cattagctcc | aatgacccga | ctgctcccgc | cgccatcaac | 1320 |
| cctaactact | ttatgttcga | atgggacggc | aagagccagg | ccggtatcgc | caagtacatc | 1380 |
| aggaagattc | tccgcagcgc | accattgaac | aaacttattg | cgaaggaaac | caagcccggt | 1440 |
| ctctctgaga | ttccggccac | tgctgcggat | gagaagtggg | ttgaatggct | caaggctaac | 1500 |
| tatcgttcca | acttccaccc | cgtcggaact | gctgccatga | tgcctcgttc | cattggtggc | 1560 |
| gttgttgata | accgtctccg | ggtctatggt | accagcaatg | ttcgcgtcgt | agatgcgtct | 1620 |
| gtcctgccct | tccaggtttg | cggccacttg | tgcagcacgc | tttatgccgt | tgccgagcgc | 1680 |
| gcttccgact | tgattaagga | ggatgcgaag | agtgcttag | | | 1719 |

<210> SEQ ID NO 6
<211> LENGTH: 1704
<212> TYPE: DNA
<213> ORGANISM: Aspergillus terreus

<400> SEQUENCE: 6

| | | | | | |
|---|---|---|---|---|---|
| atgaaatatg | attatatcgt | tattggaggc | ggtaccagcg | gtttggccgt | cgcaaaccgt | 60 |
| ctatcggagg | acccaagcgt | gaacgtactc | attctggagg | ccgtggctc | ggtctggaac | 120 |
| aatcccaatg | tcacaaacgt | gaatggctat | gggcttgcat | ttgggtctga | cattgactgg | 180 |

```
caataccagt ccgtcaacca gccatatgga ggcaacgtca gtcaagtgct gcgtgccggc    240
aaggcccttg gtggtactag tactattaac ggtatggcct atacccgcgc cgaggatgtc    300
cagatcgacg cctgggaaac cattggcaac acaggatgga cgtggaagaa tctgttccct    360
tactatcgga agagcgagaa cttcactgtc cctaccaaat cgcagacttc tcttggagcg    420
tcgtatgaag ctggagccca cggccacgag ggtccccttg acgttgcctt cactcagatc    480
gagtcgaaca acctgaccac ctacctcaac cgtaccttcc agggcatggg actcccatgg    540
actgaggacg tcaatggcgg aaagatgcgc ggctttaacc tataccectc caccgtgaat    600 cttgaggagt atgttcgcga agacgccgct cgtgcatact actggcctta caagtcccgt    660
cccaacctgc atgtcctgct caacactttt gccaaccgga ttgtgtggga cggcgaagcc    720
cgtgatggcg acatcactgc cagtggtgtc gagatcactt ccaggaacgg cactgttcgt    780
gttatcaatg cggagaagga agtcattgtc tctgccggcg ccttgaagtc cccggctatc    840
cttgaacttt ccggaattgg caaccctagc gttcttgaca agtacaacat ccccgtcaag    900
gtcaacctcc ctactgtagg tgagaacctt caggaccagg tgaacagcca catggatgcg    960
tcgggcaaca cttccatctc tggaaccaag gcagtctctt accccgatgt ctatgacgtc   1020
ttcggtgacg aagccgagtc ggtcgccaaa cagatccgtg ccagcctgaa gcaatacgcc   1080
gccgacaccg cccaggccaa cggaaacatc atgaaggccg ccgatctgga gcgtctcttc   1140
gaggtccagt atgaccttat tttcaagggc agagtcccaa ttgcagaagt cctcaactat   1200
cctggcagcg cgacgtccgt gtttgcagaa ttctgggccc tccttcccct cgctcgggga   1260
agtgttcaca tcggttcttc aaacccggtc gagtttcctg tcatcaaccc caactatttc   1320
atgctcgact gggacgcgaa gagctacgtc gccgttgcaa agtatatccg ccgctcgttc   1380
gagagctacc ctctcagcag catcgttaag gagtctaccc ctggctatga tgttatcccc   1440
cggaacgctt ctgaacagag ctggaaagaa tgggtctttg ataagaacta tcgttctaac   1500
ttccatcccg tcggcacggc tgccatgatg cctcgtgaaa ttggcggtgt cgtggacgag   1560
cgtctgaatg tctatggtac tacgaacgtc agagttgtcg atgcctcggt gcttccgttc   1620
caggtctgcg gtcatttggt gagcaccctc tacgctgtgg ccgaacgggc agcggatctc   1680
atcaaggccg atgctggtcg tcgt                                          1704
```

<210> SEQ ID NO 7
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 7

```
aacggtgcgg gattggcctt t                                               21
```

<210> SEQ ID NO 8
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 8

```
ttggccgcgg gctcggccat c                                               21
```

<210> SEQ ID NO 9
<211> LENGTH: 21
<212> TYPE: DNA

```
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 9
aacggtnnng gattggcctt t                                              21

<210> SEQ ID NO 10
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 10
ttggccnnng gctcggccat c                                              21

<210> SEQ ID NO 11
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 11
gcctttgcgt cggccatcga c                                              21

<210> SEQ ID NO 12
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 12
gttctggcgg ctggtaaggc c                                              21

<210> SEQ ID NO 13
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 13
attgacgcgt ggcagaaact t                                              21

<210> SEQ ID NO 14
<211> LENGTH: 24
<212> TYPE: DNA
<213> ORGANISM: Artificial sequence
<220> FEATURE:
<223> OTHER INFORMATION: chemically-synthesized primer

<400> SEQUENCE: 14
aacttcgcgc accccgtcgg aact                                           24

<210> SEQ ID NO 15
<211> LENGTH: 21
<212> TYPE: DNA
```

```
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 15
gcctttnnnt cggccatcga c                                              21

<210> SEQ ID NO 16
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 16
gttctgnnng ctggtaaggc c                                              21

<210> SEQ ID NO 17
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 17
attgacnnnt ggcagaaact t                                              21

<210> SEQ ID NO 18
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 18
tccaacnnnc accccgtcgg a                                              21

<210> SEQ ID NO 19
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 19
aaacagttag ttctgcgtgc t                                              21

<210> SEQ ID NO 20
<211> LENGTH: 21
<212> TYPE: DNA
<213> ORGANISM: Artificial sequence
<220> FEATURE:
<223> OTHER INFORMATION: chemically-synthesized primer
```

```
<400> SEQUENCE: 20
caagttgaac gtgctggtaa g                                              21

<210> SEQ ID NO 21
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 21
acccgctcag aggatgtcca g                                              21

<210> SEQ ID NO 22
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 22
cgttcctctt tccaccccgt c                                              21

<210> SEQ ID NO 23
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 23
aaacagnnng ttctgcgtgc t                                              21

<210> SEQ ID NO 24
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 24
caagttnnnc gtgctggtaa g                                              21

<210> SEQ ID NO 25
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 25
acccgcnnng aggatgtcca g                                              21

<210> SEQ ID NO 26
<211> LENGTH: 21
<212> TYPE: DNA
```

```
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 26
cgttccnnnt tccaccccgt c                                              21

<210> SEQ ID NO 27
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 27
gctaacnnnt atggattggc c                                              21

<210> SEQ ID NO 28
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 28
ggttatnnnt tggcctttgg c                                              21

<210> SEQ ID NO 29
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 29
tttggcnnng ccatcgactg g                                              21

<210> SEQ ID NO 30
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 30
aactacnnna tgttcgaatg g                                              21

<210> SEQ ID NO 31
<211> LENGTH: 21
<212> TYPE: DNA
```

```
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 31
ggcggcnnna gtggtcttgt g                                              21

<210> SEQ ID NO 32
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 32
ggcacannng gtcttgtggt c                                              21

<210> SEQ ID NO 33
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 33
ccggacnnna ccaacgctaa c                                              21

<210> SEQ ID NO 34
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 34
gacgtannna acgctaacgg t                                              21

<210> SEQ ID NO 35
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 35
ggaggannna gtacaatcaa t                                              21

<210> SEQ ID NO 36
<211> LENGTH: 24
<212> TYPE: DNA
```

<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 36
ggaggannna gtacaatcaa tgga                                              24

<210> SEQ ID NO 37
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 37
aatggannng cctatacccg c                                                 21

<210> SEQ ID NO 38
<211> LENGTH: 24
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 38
ggaatgnnnt atacccgcgc agag                                              24

<210> SEQ ID NO 39
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 39
ttgcttnnnt tcgcccgtgg c                                                 21

<210> SEQ ID NO 40
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 40
cccttcnnng cccgtggcaa c                                                 21

<210> SEQ ID NO 41
<211> LENGTH: 21
<212> TYPE: DNA

```
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 41
ttcgccnnng gcaacatcca c                                              21

<210> SEQ ID NO 42
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(8)
<223> OTHER INFORMATION: n is a, c, g, or t

<400> SEQUENCE: 42
ctcaagnnsa actatcgttc c                                              21

<210> SEQ ID NO 43
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 43
aaggctnnnt atcgttccaa c                                              21

<210> SEQ ID NO 44
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 44
tatcgtnnna acttccaccc c                                              21

<210> SEQ ID NO 45
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 45
tccaacnnnc accccgtcgg a                                              21

<210> SEQ ID NO 46
<211> LENGTH: 21
<212> TYPE: DNA
```

```
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 46
ttccacnnng tcggaactgc t                                              21

<210> SEQ ID NO 47
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 47
caccccnnng gaactgctgc c                                              21

<210> SEQ ID NO 48
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(8)
<223> OTHER INFORMATION: n is a, c, g, or t

<400> SEQUENCE: 48
cgcgtcnnsg atgcgtctgt c                                              21

<210> SEQ ID NO 49
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 49
ttccagnnnt gcggccactt g                                              21

<210> SEQ ID NO 50
<211> LENGTH: 21
<212> TYPE: DNA
<213> ORGANISM: Artificial sequence
<220> FEATURE:
<223> OTHER INFORMATION: chemically-synthesized primer
<220> FEATURE:
<221> NAME/KEY: misc_feature
<222> LOCATION: (7)..(9)
<223> OTHER INFORMATION: n is a, c, g, or t

<400> SEQUENCE: 50
gccgtgnnnt ccgaattctg g                                              21

<210> SEQ ID NO 51
<211> LENGTH: 37
<212> TYPE: DNA
```

```
<213> ORGANISM: Artificial sequence
<220> FEATURE:
<223> OTHER INFORMATION: chemically-synthesized primer

<400> SEQUENCE: 51
gcagcgcgac gtccgtgagc gcagaattct gggccct                              37

<210> SEQ ID NO 52
<211> LENGTH: 35
<212> TYPE: DNA
<213> ORGANISM: Artificial sequence
<220> FEATURE:
<223> OTHER INFORMATION: chemically-synthesized primer

<400> SEQUENCE: 52
gcagcgcgac gtccgtgatt gcagaattct gggcc                                35

<210> SEQ ID NO 53
<211> LENGTH: 37
<212> TYPE: DNA
<213> ORGANISM: Artificial sequence
<220> FEATURE:
<223> OTHER INFORMATION: chemically-synthesized primer

<400> SEQUENCE: 53
gcagcgcgac gtccgtggtg gcagaattct gggccct                              37

<210> SEQ ID NO 54
<211> LENGTH: 21
<212> TYPE: DNA
<213> ORGANISM: Artificial sequence
<220> FEATURE:
<223> OTHER INFORMATION: chemically-synthesized primer

<400> SEQUENCE: 54
ggaaacgtgg tgtcctccga a                                               21
```